United States Patent
Ryaby et al.

(10) Patent No.: US 10,238,867 B2
(45) Date of Patent: Mar. 26, 2019

(54) PULSED ELECTROMAGNETIC FIELD TISSUE STIMULATION TREATMENT AND COMPLIANCE MONITORING

(71) Applicant: Orthofix Inc., Lewisville, TX (US)

(72) Inventors: James T. Ryaby, Lewisville, TX (US); Mamak Monica Keramat, Lewisville, TX (US); Lesley Allen Bowling, Lewisville, TX (US); Bobby Don Harris, Lewisville, TX (US); James Sterling Denton, Lewisville, TX (US); Philip Hartley Garman, Lewisville, TX (US); Jeffrey James Culhane, Lewisville, TX (US); Jonelle Matilda Juricek, Lewisville, TX (US)

(73) Assignee: Orthofix Inc., Lewisville, TX (US)

( * ) Notice: Subject to any disclaimer, the term of this patent is extended or adjusted under 35 U.S.C. 154(b) by 0 days.

(21) Appl. No.: 15/783,072

(22) Filed: Oct. 13, 2017

(65) Prior Publication Data

US 2018/0104484 A1  Apr. 19, 2018

Related U.S. Application Data

(60) Provisional application No. 62/409,014, filed on Oct. 17, 2016.

(51) Int. Cl.
*A61N 1/32* (2006.01)
*A61N 1/36* (2006.01)
(Continued)

(52) U.S. Cl.
CPC .............. *A61N 1/326* (2013.01); *A61N 1/08* (2013.01); *A61N 1/36003* (2013.01);
(Continued)

(58) Field of Classification Search
CPC ................ A61N 1/326; A61N 1/36003; A61N 1/36025; A61N 1/37211; A61N 1/0476; A61N 2/02
See application file for complete search history.

(56) References Cited

U.S. PATENT DOCUMENTS

| 5,743,844 A | 4/1998 | Tepper et al. |
| 6,024,691 A | 2/2000 | Tepper et al. |

(Continued)

OTHER PUBLICATIONS

International Searching Authority, United States Patent Office, "International Search Report and The Written Opinion of the International Searching Authority," for PCT/US2017/056765, dated Dec. 21, 2017, 7 pages.

*Primary Examiner* — Christine H Matthews
*Assistant Examiner* — Joshua Daryl D Lannu
(74) *Attorney, Agent, or Firm* — Haynes and Boone, LLP

(57) ABSTRACT

A system and method for PEMF tissue engineering enhances musculoskeletal tissue stimulation by monitoring treatment for compliance with treatment regimens. A PEMF device includes sensors that detect attributes indicating whether the PEMF device is in use. The PEMF device also includes communication devices that connect it with other devices. The data obtained from the sensors may be used to determine a level of compliance in use of the tissue engineering device with a prescribed treatment regimen for the patient. The data is transferred via a paired UE to a remote server. The remote server stores the data in a database and periodically generates compliance reports. The compliance reports are shared with subscribing access devices including the prescribing physician. The UE pairing with the PEMF device maintains a treatment calendar and dynamically modifies reminders based on current treatment status. The treatment regimen may be updated and sent to the PEMF device.

15 Claims, 9 Drawing Sheets

(51) Int. Cl.
  *A61N 1/372* (2006.01)
  *A61N 1/40* (2006.01)
  *A61N 1/08* (2006.01)
  A61N 1/04 (2006.01)
  A61N 2/02 (2006.01)
  A61N 1/02 (2006.01)

(52) U.S. Cl.
  CPC ........... *A61N 1/36025* (2013.01); *A61N 1/40* (2013.01); *A61N 1/025* (2013.01); *A61N 1/0476* (2013.01); *A61N 1/37211* (2013.01); *A61N 2/02* (2013.01)

(56) References Cited

U.S. PATENT DOCUMENTS

| | | |
|---|---|---|
| 6,132,362 A | 10/2000 | Tepper et al. |
| 6,261,221 B1 | 7/2001 | Tepper et al. |
| 2003/0167078 A1* | 9/2003 | Weisner ............. A61N 1/37217 607/60 |
| 2006/0122660 A1* | 6/2006 | Boveja ............... A61N 1/36007 607/40 |
| 2009/0216068 A1 | 8/2009 | Thomas et al. |
| 2013/0106994 A1* | 5/2013 | Sharp ................ G06K 9/00362 348/43 |
| 2014/0221726 A1 | 8/2014 | Pilla et al. |
| 2016/0106994 A1 | 4/2016 | Crosby et al. |

* cited by examiner

PULSED ELECTROMAGNETIC FIELD TISSUE STIMULATION TREATMENT AND COMPLIANCE MONITORING

CROSS REFERENCE TO RELATED APPLICATIONS

The present application claims priority to and the benefit of the U.S. Provisional Patent Application No. 62/409,014, filed Oct. 17, 2016, which is hereby incorporated by reference in its entirety as if fully set forth below in its entirety and for all applicable purposes.

TECHNICAL FIELD

The present description relates to systems, apparatus, and methods of tissue engineering to enhance the growth of musculoskeletal tissues by monitoring treatment remotely to ensure compliance with prescribed treatment regimens.

BACKGROUND

An approach to treating various types of musculoskeletal issues involves applying pulsed electromagnetic fields (PEMF) to the general areas of the body where the musculoskeletal issues exist. PEMF involves low-energy, time-varying pulses of magnetic fields. PEMF is therapeutic to various issues including fractures, spinal fusion, ligament injuries, tendon injuries, and osteoporosis as just a few examples. PEMF has been clinically observed to benefit in stimulating tissue differentiation and/or tissue generation when performed according to prescribed measures (i.e., duration of treatment per use, intensity of treatment, number of uses over time, etc.).

A challenge arises, however, in ensuring patient compliance with prescribed measures in the treatment regimen so as to achieve the desired therapeutic outcome. At best, the physician tasked with treating the musculoskeletal issue can monitor whether the tissue engineering device (that provides the PEMF treatment) was activated in a given day or not. But this is not always tantamount to the patient actually complying with the treatment regimen. For example, the tissue engineering device may be turned on but not actually applied to the tissue of the patient (e.g., activated and left on a chair, tabletop, etc.).

This can result in significantly degraded treatment outcomes, whether by delaying the efficacy of treatment over time or generally causing sub-par results. A need exists to improve the clinical success rate of PEMF tissue engineering devices when treating musculoskeletal tissue according to proven regimens, all while still providing an energy-efficient tissue engineering device that is convenient for the patient to use so as to facilitate prescribed use.

BRIEF DESCRIPTION OF THE DRAWINGS

The present disclosure is best understood from the following detailed description when read with the accompanying figures.

DETAILED DESCRIPTION

Figure 1:
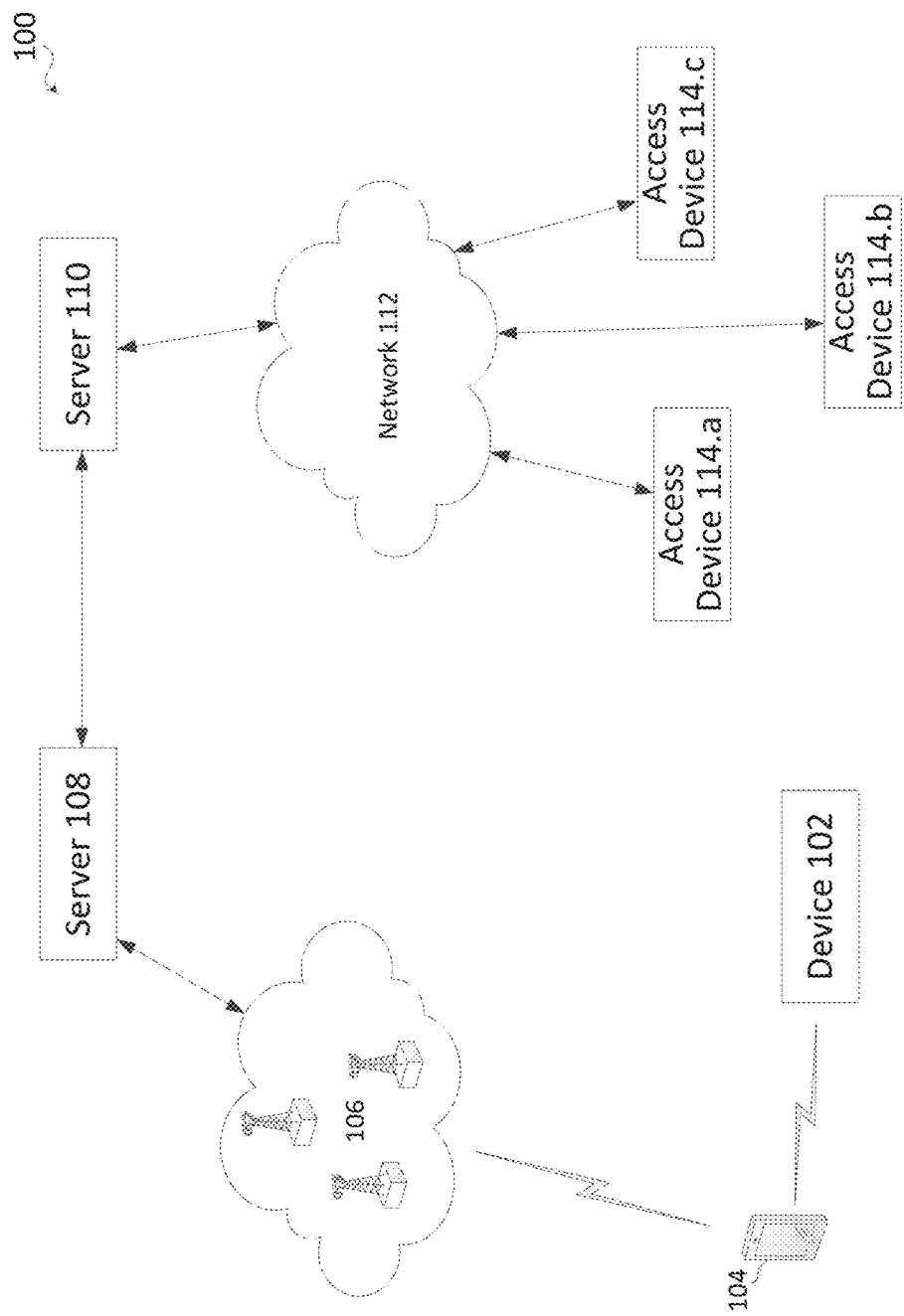
FIG. 1 is an organizational diagram of an exemplary treatment and monitoring system architecture according to aspects of the present disclosure.

All examples and illustrative references are non-limiting and should not be used to limit the claims to specific implementations and embodiments described herein and their equivalents. For simplicity, reference numbers may be repeated between various examples. This repetition is for clarity only and does not dictate a relationship between the respective embodiments. Finally, in view of this disclosure, particular features described in relation to one aspect or embodiment may be applied to other disclosed aspects or embodiments of the disclosure, even though not specifically shown in the drawings or described in the text.

Various embodiments include systems, methods, and machine-readable media for tissue engineering to enhance the growth of musculoskeletal tissues by monitoring treatment remotely to ensure compliance with prescribed treatment regimens. A tissue engineering device that provides treatment to one or more musculoskeletal tissues of a patient is equipped with networking devices that allow it to connect with one or more devices. For example, the tissue engineering device is capable of pairing with another device, identified as a user equipment (UE) herein, such as via a Bluetooth, wired, or near field communication technology. The tissue engineering device is further equipped with one or more sensors that monitor different aspects of operation of the tissue engineering device. The data obtained from the sensors (historical usage data and/or current usage data, for example) may be used to determine a level of compliance in use of the tissue engineering device with a prescribed treatment regimen for the patient.

Over time, the sensors' monitored data is transferred to the UE when the UE pairs with the tissue engineering device. The UE relays the monitored data, typically stripped of patient identifying information in some embodiments (and/or encrypted), to a remote server. The remote server may maintain a database of different patient profiles associated with tissue engineering devices and prescribed treatment regimens. As the monitoring data is received at the remote server, the remote server associates the data with the proper patient profile and stores the monitoring data as part of that profile. Periodically, the remote server generates a compliance report for that patient based on the monitoring data aggregated in the database. This compliance report may identify a level of compliance, and details associated therewith, of the use of the tissue engineering device for the patient to the prescribed treatment regimen. The remote server may send, or otherwise make available, the compliance report to one or more subscribing access devices (e.g., associated with the physician or other interested parties).

Further, the UE that pairs with the tissue engineering device may also maintain a calendar for treatment based on the prescribed treatment regime as well as provide for other maintenance. For example, reminders may be set in the calendar for treatment. During a given treatment period (e.g., a day), the UE may track monitoring data as it is received from the tissue engineering device and use that to modify any scheduled reminder (e.g., to change the content of the reminder, an intensity of the reminder, etc.). In this manner, the UE may dynamically adjust the reminders to the prevailing conditions of use for the given periodic application of treatment. Further, the UE may provide contact information for the prescribing physician, healthcare provider, and/or a representative for the manufacturer of the tissue engineering device, as well as links to one or more online access systems such as one that allows the patient to modify their identifying information in the remote server's database.

The prescribing physicians, by accessing the compliance reports, may send messages to the patient to encourage improved compliance and/or other important information, as well as provide additional data points on which to base changes to the prescribed treatment regimen. The messages/updates to the treatment regimen may be submitted via an access portal to the remote server. The remote server may update its records and forward the message/update to the UE and the tissue engineering device.

As a result of the foregoing, embodiments of the present disclosure improve the field of pulsed electromagnetic field therapy for tissue engineering, such as for tissue differentiation and/or growth stimulation of tissue. In particular, embodiments of the present disclosure improve the transparency of treatment compliance so that more efficacious treatment regimens may be provided and prescribed to patients, whether at the onset of treatment or dynamically during treatment. The tissue engineering device itself may therefore be tuned to operate more efficiently for a given indication within a prescribed period of time as is now otherwise possible. This may therefore further improve clinical success rates of tissue engineering devices while still providing an energy-efficient tissue engineering device that is convenient for the patient to use according to prescribed usage.

FIG. 1 illustrates an organizational diagram of an exemplary treatment and monitoring system architecture 100 according to aspects of the present disclosure. The treatment and monitoring system architecture 100 may include one or more tissue engineering devices 102, one or more user equipment ("UE," also referred to herein as user devices) 104, a wireless network 106, a remote server 108, a remote server 110, a network 112 (that may be part of or separate from the wireless network 106), and one or more access devices 114 (also referred to herein as subscribing devices).

The tissue engineering device 102 may be a PEMF device or an ultrasound device, a combined magnetic field device, or a direct current device to name some examples of tissue engineering devices to which embodiments of the present disclosure apply. The tissue engineering device 102 provides therapeutic treatment (e.g., PEMF or ultrasound, a combination, etc.) to musculoskeletal tissues of a patient. As used herein, musculoskeletal tissue may refer to any of a variety of tissues of a patient, including bone tissue, tendons, cartilage, etc., and/or some combination thereof. The tissue engineering device 102 may be designed and manufactured to provide specific forms of treatment to specific tissues, for example to treat fractures of bones of a patient, or as an adjunctive treatment option for cervical fusion, or spinal fusion as just a few examples. The tissue engineering device 102 may include multiple sensors such as infrared (IR) or other type of proximity sensor as well as accelerometers, gyroscopes, and/or GPS units to detect motion as an indicator of use. The tissue engineering device 102 is exemplary of multiple such devices that may be included in the exemplary treatment and monitoring system architecture 100 (i.e., just one is illustrated for simplicity of discussion). In other words, the server 108 may maintain a database of multiple tissue engineering devices 102 associated with multiple patients.

The tissue engineering device 102 may be in communication with a UE 104. There may be a plurality of UEs 104 in the treatment and monitoring system architecture 100, where some subset of UEs 104 may at least periodically come within communication range of one or more tissue engineering devices 102 and communicate with them according to embodiments of the present disclosure. The UE 104 may also be referred to as a terminal, a mobile station, a subscriber unit, etc. The UE 104 may be a cellular phone, a smartphone, a personal digital assistant, a wireless modem, a laptop computer, a tablet computer, a drone, an entertainment device, a hub, a gateway, an appliance, a wearable, peer-to-peer and device-to-device components/devices (including fixed, stationary, and mobile), Internet of Things (IoT) components/devices, and Internet of Everything (IoE) components/devices, etc.

According to embodiments of the present disclosure, the UE 104 may periodically pair with one or more tissue engineering devices 102 to receive treatment data (also referred to as sensor data, usage data, or monitored data herein) from the tissue engineering devices 102 and/or provide treatment regimen updates from the server 108 when those are received. With the data, the UE 104 may, when associated with the patient receiving treatment from the tissue engineering device 102 or someone in association with the patient, provide various interactive features to assist in promoting treatment according to the prescribed regimen. This may include calendar functions and associated reminders, smart calendaring (e.g., modifying reminders based on data obtained about actual treatment already performed), psychological encouragement such as with games or other motivational factors promoting the patient to engage in the prescribed treatment regimen, resource provision (e.g., contact information for one or more of sales representatives, manufacturer representatives, treating physician, etc.), and displays identifying remaining treatment time for a given application according to the treatment regimen, just to name some examples.

The wireless network 106 is one example of a network to which aspects of the present disclosure apply. The wireless network 106 may include one or more base stations that communicate with the UE 104. A UE 104 may communicate with one or more base stations in the wireless network 106 via an uplink and a downlink. The downlink (or forward link) refers to the communication link from the base station to the UE 104. The uplink (or reverse link) refers to the communication link from the UE 104 to the base station. The base stations in the wireless network 106 may also communicate with one another, directly or indirectly, over wired and/or wireless connections, as well as with the server 108 over wired and/or wireless connections. A base station in the wireless network 106 may also be referred to as an access point, base transceiver station, a node B, eNB, etc.

Although illustrated with the UE 104 acting as a relay to the tissue engineering device 102, for example to conserve on energy at the tissue engineering device 102, in some embodiments the tissue engineering device 102 may establish its own connection to the wireless network 106 to communicate with the server 108 without the assistance of the UE 104 (but may still establish a separate connection with the UE 104 according to aspects of the present disclosure).). Although illustrated as wireless, the wireless network 106 may also be, or include, wired connections (whether among different nodes, with the UE 104 and/or tissue engineering device 102, etc.).

The server 108 may be a tissue engineering treatment regimen server that provides both a database to house current and historical usage/treatment data, treatment regimens, device profiles, patient profiles, physician profiles, manufacturer profiles, and/or sales representative profiles, as well as an additional intermediary between the tissue engineering devices 102, UEs 104 that include modules/applications for patient and interested party interaction, manufacturer server 110 (if involved), and/or access devices 114. The server 108 may update its database once it receives treatment data from tissue engineering devices 102 (whether via the UE 104 as a relay/intermediary or not), and use that data to generate compliance reports. This may be done by aggregating the data over time, e.g. on a daily basis or some other period of time, on demand, or forwarding in reports on a rolling basis in real time or near-real time. For example, the server 108 may analyze and characterize the data aggregated over time (e.g., both over a period of time and over multiple periods of time) to generate fields in the compliance report that identify likely amounts and types of activity sustained by the tissue engineering device 102 during the period (or periods) during the treatment regimen. The server 108 may communicate with the wireless network 106 via its own wireless connection and/or via one or more wired connections (e.g., backhaul connections, one or more wired network such as Internet connections, etc.) as well as with the server 110/network 112 via one or more wired and/or wireless connections.

The server 110 may be a server hosted by the manufacturer of the tissue engineering device 102 (and/or provider of the module or application with which the patient interacts on the UE 104, or by the physician on the access devices 114). For example, the server 110 may provide a portal for subscribing parties to access to review treatment regimens, modify those regimens (where permissions are given), update device profile parameters, etc. In some embodiments, the functions and purposes of the server 110 may be implemented together with the server 108, or alternatively be not included.

One or more access devices 114 are in communication with the server 110 (and the server 108). In FIG. 1, these are illustrated as access devices 114.a, 114.b, and 114.c—this is representative of any number of access devices 114. The access devices 114 are in communication with the server 110 via the network 112, which may be any wired, wireless, or combination thereof network. As noted above, the access devices 114 may be associated with parties that have subscribed to access to the server 110 and the server 108. The access devices 114 may include UEs such as discussed above, tablet computers, laptop computers, desktop computers, servers, etc. that provide access to subscribing parties. The access may include receiving compliance reports, sending messages back to the UE 104 and/or tissue engineering devices 102, and/or sending treatment modifications to the server 110 and/or server 108 and on to the tissue engineering devices 102. Further, the UE 104 may be one of many access devices 114, in addition to those associated with other parties as well.

For example, a physician providing the treatment regimen for a patient using a tissue engineering device 102 may subscribe at a portal provided by the server 110 (or the server 108) to receive compliance reports from the server 108 as they are provided, select the frequency of those compliance reports, input new treatment regimens for already-registered or newly-added tissue engineering devices 102, and/or modify existing treatment regimens (e.g., depending upon access privileges for the given subscriber). As another example, a relative of the patient may be allowed to subscribe for compliance reports, or some redacted version of the compliance reports, so as to provide additional incentive to the patient or their loved ones to support compliance with the treatment regimen.

As another example, as a patient uses (or doesn't use) the tissue engineering device 102 as prescribed, sensors that are part of the tissue engineering device 102 output monitoring results (e.g., ranging from actual measurements for interpretation by a processor to a binary output, such as yes/no for whether the feature the sensor is designed for was triggered or not during a given time period). The tissue engineering device 102 may further display a general treatment compliance to a treatment regimen (e.g., expressed as a percentage). If a UE 104 is already paired with the tissue engineering device 102, then the data may be transmitted as soon as it is output (e.g., real-time, while in other examples the data may be transmitted according to a schedule such as to conserve battery power). Likewise, if the tissue engineering device 102 is in communication with the server 108 without the aid of the UE 104, then the data may be transmitted as soon as it is output. Alternatively, where a UE 104 is not paired with the tissue engineering device 102 as data regarding compliance is output from the sensors, and the tissue engineering device 102 does not bypass the UE 104 in communicating with the server 108, then the tissue engineering device 102 may store the data locally as it is output.

The storage may continue until it is periodically within range with a UE 104 that can pair with the tissue engineering device 102 to receive the data (and/or a scheduled time to transmit the data to the UE 104 or the server 108). In some embodiments, the UE 104 may be the patient's UE, and therefore may frequently be in proximity with the tissue engineering device 102 (and, when not, an alert on the UE 104 can remind the patient to bring them within range to pair and share data). As another example, a sales representative or other representative of the manufacturer, physician's office, or other entity may periodically visit different patients (or the patients visit them) and reach a sufficient proximity to intentionally pair with the tissue engineering devices 102 with which the UE 104 of the representative comes in range. However the data is retrieved/received from the tissue engineering device 102, once it is compiled into a report the physician and other subscribed users may receive it and provide additional instruction/comments thereto for the benefit of the patient.

The storing of the sensor data until pairing occurs may also occur in embodiments where a transceiver capable of pairing with a UE 104 is located external to the tissue engineering device 102 (e.g., a power supply or a docking station). The tissue engineering device 102 may store the data locally until connected again to such an external transceiver, at which time data may continue being stored until paired, via the external transceiver, to a UE 104 as discussed above and further below.

At the UE 104, the data received may be further analyzed to discover broader trends for the patient. For example, the UE 104 may determine using one or more embedded algorithms whether the patient is sedentary or mobile during each treatment session (based on the data from the tissue engineering device 102). This may be aggregated over time and analyzed by the UE 104 to determine further whether the patient is generally more or less mobile over a period of time (such as days, weeks, or months). These trends may be further passed on, such as part of the monitoring data, to the server 108. At the server 108, in addition to generating compliance reports generally, the server 108 may further analyze the monitoring data it receives to compare the patient's results to the results of similar patients' data. That similar data may be made available through other sources, such as public registers and/or other patient recorded outcomes.

Figure 2:
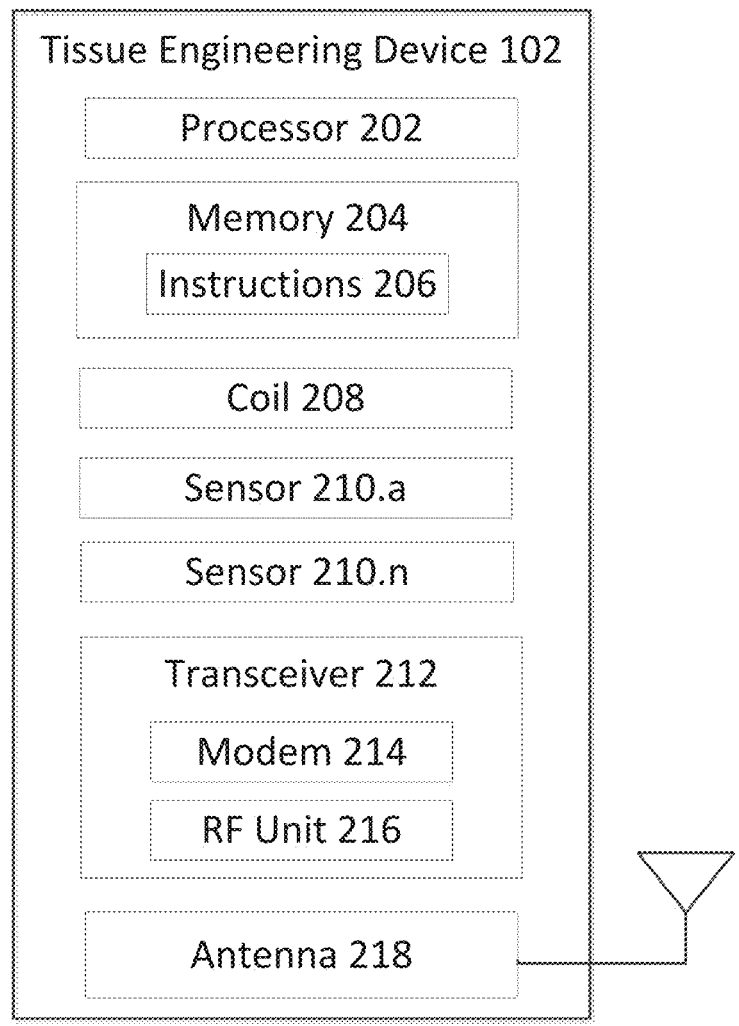
FIG. 2 is an organizational diagram of an exemplary tissue engineering device according to aspects of the present disclosure.

FIG. 2 is an organizational diagram of an exemplary tissue engineering device 102 as introduced in FIG. 1, according to aspects of the present disclosure. In the example of FIG. 2, the tissue engineering device 102 may be a PEMF device having one of many configurations within the treatment and monitoring system architecture 100 of FIG. 1 (in embodiments where the tissue engineering device 102 is an ultrasound device, the coil 208 may be replaced with an ultrasound transducer; the description here is of the PEMF device for FIG. 2 and other figures for simplicity of discussion). The tissue engineering device 102 may include a processor 202, a memory 204, a coil 208, sensors 210.*a* through 210.*n*, a transceiver 212 (including a modem 214 and RF unit 216), and an antenna 218. These elements may be in direct or indirect communication with each other, for example via one or more buses.

The processor 202 may have various features as a specific-type processor. For example, these may include a central processing unit (CPU), a digital signal processor (DSP), an application-specific integrated circuit (ASIC), a controller, a field programmable gate array (FPGA) device, another hardware device, a firmware device, or any combination thereof configured to perform the operations described herein with reference to the tissue engineering devices 102 introduced in FIG. 1 above. The processor 202 may also be implemented as a combination of computing devices, e.g., a combination of a controller and a microprocessor, a plurality of microprocessors, one or more microprocessors in conjunction with a DSP core, or any other such configuration.

The memory 204 may include a cache memory (e.g., a cache memory of the processor 302), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory 204 may include a non-transitory computer-readable medium. The memory 204 may store instructions 206. The instructions 206 may include instructions that, when executed by the processor 202, cause the processor 202 to perform operations described herein with reference to a tissue engineering device 102 in connection with embodiments of the present disclosure. The terms "instructions" and "code" may include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The coil 208 provides PEMF pulses according to embodiments of the present disclosure. Control electronics for the coil 208 may be included as part of the processor 202 (e.g., in combination with instructions 206 in the memory 204) or alternatively be separate hardware. The coil 208 may be constructed with multiple windings of any suitable material for generating electromagnetic fields according to the treatment regimen as provided by the processor 202. For example, the processor 202 may access the treatment regimen stored in the memory 204 that causes current to pass through the coil 208, including according to a set rise and/or fall time, duty cycle, amplitude, frequency, etc. for the current so as to generate electromagnetic frequency pulses of a desired duration, size, shape, and frequency. Further, the treatment regimen may be modified via one or more updates received from the server 108, whether via the UE 104 or other network components/connections.

The treatment regimen may include programmed pulse trains, where each pulse train includes a specified number of pulses with specified duration (and rise/fall times with specified amplitude), and repeated in a fixed pattern over time (i.e., duty cycle) over the course of a given treatment period. There may be a number of treatment periods specified over a longer duration of time. For example, a given treatment period may be specified to last for several hours each day—the treatment period may refer to the two hour duration specified per day, which may be repeated for a longer duration such as over weeks or months. A heartbeat LED may indicate a treatment status for the periodic application of the PEMF over the long-term duration.

Multiple sensors 210.*a* through 210.*n* represent any number of sensors that may monitor different aspects of operation of the tissue engineering device 102 according to embodiments of the present disclosure. For example, sensor 210.*a* may be an accelerometer. As the tissue engineering device 102 is placed on the patient, the accelerometer may sense this motion and output, e.g. when polled, periodic status indicators identifying whether motion has been detected.

For example, every 100 ms the accelerometer may be polled by the processor 202 to determine whether motion is detected; if so, the data output may be a yes (e.g., a first binary value) and if not then a no (e.g., a second binary value). Over multiple such intervals, e.g. after 3 seconds, if motion is detected with any poll of the accelerometer, then this is identified as "yes" for the 3 second chunk of time. After multiple 3 second chunks of time, e.g. after 30 seconds, if more than half of the 3 second chunks of time are identified as "yes," then the 30 second chunk of time is identified as "yes." After multiple 30 second chunks of time, e.g. after 5 minutes, if more than a quarter of the 30 second chunks are identified as "yes," then the 5 minute chunk is identified as "yes." This may again occur with a longer chunk of time, e.g. 30 minutes. These particular values for time are exemplary only; other values may be used instead. Further, the thresholds (e.g., half or a quarter) may also be changed based on the parameters of a particular system to be larger or smaller than that given in this example.

As another example, sensor 210.*n* may be an infrared sensor. The infrared sensor may be used to detect whether something is within a threshold proximity of the sensor. Therefore, the infrared sensor may be placed (one or more)

in a location of the tissue engineering device 102 intended to face the body of the patient receiving treatment. As another example of a sensor similar in intent to an infrared sensor, the tissue engineering device may include a capacitive sensor instead of or in addition to the infrared sensor.

Using the infrared sensor as an example, the infrared sensor may operate in cooperation with the accelerometer to assist in identifying whether the tissue engineering device 102 is being used in accordance with the treatment regimen. For example, the processor 202 may periodically poll the infrared device to determine whether it is detecting proximity to another object (e.g., some part of the patient). If not, then it may be concluded that even if motion is detected by the accelerometer, the tissue engineering device 102 is not being used for treatment. In contrast, if the infrared sensor indicates close proximity to an object, but the accelerometer does not detect motion above a threshold amount, then it may be inferred that the tissue engineering device 102 is not being used for treatment. This may occur, for example, where the tissue engineering device 102 is placed on some vibrating object such as a laundry machine.

As another example of a sensor, the tissue engineering device 102 may include a global positioning system (GPS) device. The GPS device may detect the location of the tissue engineering device 102 and provide that to the processor 202 for further analysis. For example, the location of the patient's preferred place of treatment may be stored and compared against whenever the coil 208 is activated. If the GPS device detects a location outside a threshold radius of the preferred place, then it may be inferred that treatment is not occurring (unless the patient expressly inputs that treatment is occurring). As another example, if the GPS device detects that the tissue engineering device 102 is moving, but the IR sensor (where included) detects that the tissue engineering device 102 is not in sufficient proximity to another object (e.g., the patient) then it is inferred that treatment is not occurring.

As another example of a sensor, the tissue engineering device 102 may include an impedance monitor sensor (also referred to as simply an impedance monitor). The impedance monitor may use impedance spectroscopy to identify different types of tissue of the patient and correlate that to the known types of tissues present in the different stages of healing. This data may be included to assist in monitoring the progress of healing, which may be correlated to the level of compliance that the patient has over time with the tissue engineering device 102. The impedance monitor may be an ultrasound or electromagnetic field.

As an alternative to the impedance monitor sensor, more generally the impedance monitor sensor may be a type of sensor to monitor healing. This may include an impedance monitor sensor as noted above. Alternatively, it may include a sensor such as x-rays (e.g., low-energy x-rays), ultrasound, electrical impedance tomography, or other approaches to measure healing or density such as measuring electrical and/or electroacoustic properties of healing tissue, etc. (e.g., some combination of the above sensor types). All of these approaches may be referred to herein generically under "impedance monitoring" and "impedance monitoring sensors" for purposes of simplicity of discussion.

These are a few examples of sensors 210.*a* through 210.*n* that may be included with the tissue engineering device 102, and which may be used to output data (historical and/or current) that assists in determining an amount of progress for a current application period as well as multiple application periods over time. Any combination of the sensors may be included in a given tissue engineering device 102, or all of them in cooperation with each other.

As shown, the transceiver 212 may include the modem subsystem 214 and the radio frequency (RF) unit 216. The transceiver 212 can be configured to communicate bi-directionally with other devices, such as UEs 104 and/or other network elements such as those in the wireless network 106. The modem subsystem 214 may be configured to modulate and/or encode data according to any of a variety of coding schemes. The RF unit 216 may be configured to process (e.g., perform analog to digital conversion or digital to analog conversion, etc.) modulated/encoded data from the modem subsystem 214 (on outbound transmissions) or of transmissions originating from another source such as a UE 104. Although shown as integrated together in transceiver 212, the modem subsystem 214 and the RF unit 216 may be separate devices that are coupled together to enable the tissue engineering device 102 to communicate with other devices.

The RF unit 216 may provide the modulated and/or processed data, e.g. data packets (or, more generally, data messages that may contain one or more data packets and other information), to the antenna 218 for transmission to one or more other devices such as the UE 104. This may include, for example, transmission of sensor data (either raw or processed, such as "yes" or "no" data over time) according to embodiments of the present disclosure. The antenna 218 may further receive data messages transmitted from other devices and provide the received data messages for processing and/or demodulation at the transceiver 212. Although FIG. 2 illustrates antenna 218 as a single antenna, antenna 218 may include multiple antennas of similar or different designs in order to sustain multiple transmission links.

In some embodiments the transceiver 212 may be a Bluetooth low energy (BLE) device. In other embodiments, the transceiver 212 may be a USB port, an Ethernet port, a cell module (e.g., LTE, 5G, etc.), a WiFi module, a ZigBee module, or a near field communication (NFC) module. The tissue engineering device 102 may further include multiple transceivers 212, such as a BLE device as well as a cell module to provide multiple forms of communication. In embodiments where multiple forms of communication are possible, the tissue engineering device 102 may communicate with different devices concurrently. For example, the tissue engineering device 102 may pair with a first UE 104 via a first connection, such as BLE, and also pair with a second UE 104 via a second connection such as NFC. Further or alternatively, the tissue engineering device 102 may communicate with the network 106 via a cell module (where included) concurrent to pairing with one or more UEs 104.

As another example, the transceiver 212 (or multiple transceivers 212) may be coupled with the tissue engineering device 102 via one or more connections. For example, the transceiver 212 may be included with some accessory to the tissue engineering device 102, such as a charging power supply or a docking station for the tissue engineering device 102. The tissue engineering device 102 may couple with the accessory via a cable or other connection, such as a USB cable. Thus, in embodiments where the transceiver 212 is included with an accessory, the sensor data may be kept by the tissue engineering device 102 (e.g., in the memory 204) until the tissue engineering device 102 is connected with the accessory, which may occur during a treatment or in between treatments, or both. Upon connection, the transceiver 212 may transfer sensor data to the paired UE 104/network 106 according to the type of transceiver included. When included in an accessory, the size and battery consumption of the tissue engineering device may be further minimized.

Figure 3:
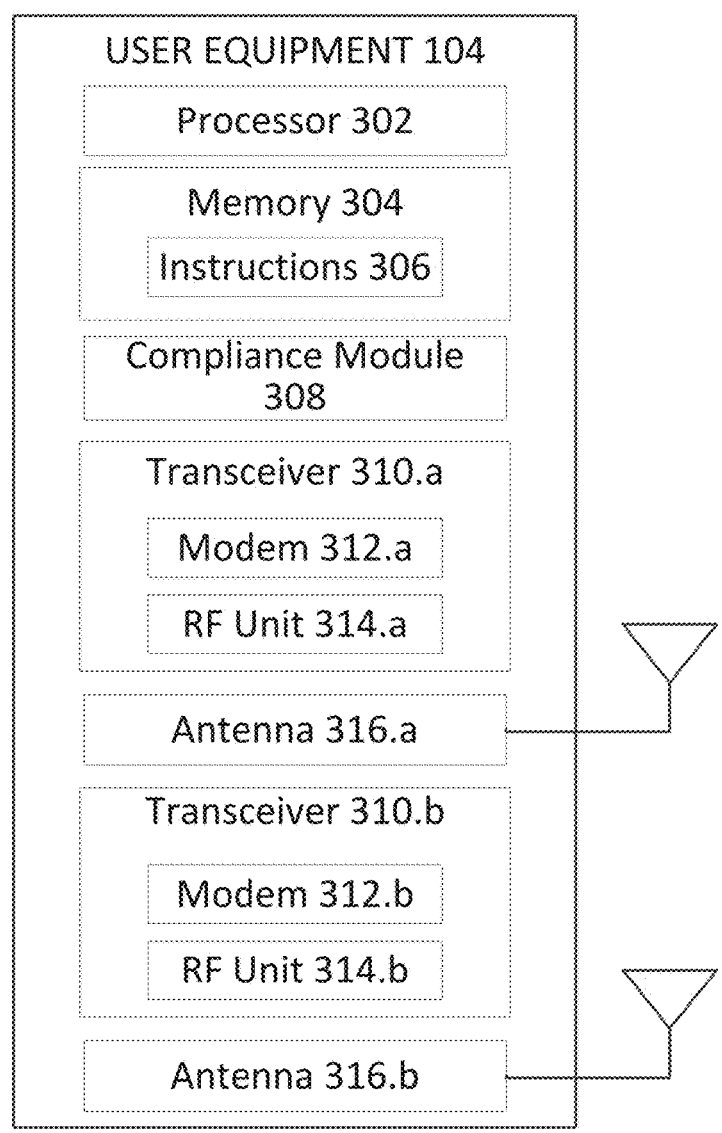
FIG. 3 is an organizational diagram of an exemplary user device according to aspects of the present disclosure.

Turning now to FIG. 3, an organizational diagram 300 of an exemplary user device (UE) 104 (e.g. as introduced in FIG. 1) is illustrated according to aspects of the present disclosure. The UE 104 may be any of a variety of devices as discussed above with respect to FIG. 1. The UE 104 may include a processor 302, a memory 304, a compliance module 308, transceivers 310.a and 310.b, and antennae 316.a and 316.b. These elements may be in direct or indirect communication with each other, for example via one or more buses.

The processor 302 may have various features. For example, these may include a central processing unit (CPU), a digital signal processor (DSP), an application-specific integrated circuit (ASIC), a controller, a field programmable gate array (FPGA) device, another hardware device, a firmware device, or any combination thereof configured to perform the operations described herein with reference to the UEs 104 introduced in FIG. 1 above. The processor 302 may also be implemented as a combination of computing devices, e.g., a combination of a controller and a microprocessor, a plurality of microprocessors, one or more microprocessors in conjunction with a DSP core, or any other such configuration.

The memory 304 may include a cache memory (e.g., a cache memory of the processor 302), RAM, MRAM, ROM, PROM, EPROM, EEPROM, flash memory, solid state memory device, hard disk drives, other forms of volatile and non-volatile memory, or a combination of different types of memory. In some embodiments, the memory 304 may include a non-transitory computer-readable medium. The memory 304 may store instructions 306. The instructions 306 may include instructions that, when executed by the processor 302, cause the processor 302 to perform operations described herein with reference to a UE 104 in connection with embodiments of the present disclosure.

The compliance module 308 may be an application executed by the processor 302, for example an application downloaded from the server 108 (or the server 110 as some examples). The compliance module 308 may include multiple features designed to both monitor the use of the tissue engineering device 102 as well as encourage compliance with a prescribed treatment regimen. For example, the compliance module 308 may store treatment regimens/updates to treatment regimens that are meant for a tissue engineering device 102 with which the UE 104 is paired (or has been paired with in the past). Further, the compliance module 308 may store other data associated with the patient's return to health. For example, the compliance module 308 may periodically prompt the user to provide pain scale data (i.e., a rating by the using of what level of pain (if any) the user is feeling). This may be captured on a visual pain scale, a graduated numeric scale, etc. as just some examples. Other patient health information related to progression of healing or therapy may include recording daily activity levels, adherence to physical therapy protocols or taking prescribed medications, some combination of the above, etc. The compliance module 308 may cause a transceiver 310 to transmit this information (all or some of it) to the paired tissue engineering device 102 at the next (or a timed) opportunity.

For example, the transceiver 310.a (including modem 312.a and RF unit 314.a, coupled to antenna 316.a) may be a Bluetooth (or Bluetooth LE) device configured to pair with other BLE devices, such as when the transceiver 212 associated with tissue engineering device 102 is another BLE device. The transceiver 310.a may alternatively be, or additionally include, a USB port, an Ethernet port, a cell module (e.g., LTE, 5G, etc.), a WiFi module, a ZigBee module, or a near field communication (NFC) module. The UE 104 may further include a transceiver 310.b, including modem 312.b and RF unit 314.b with similar functions as discussed above with respect to transceiver 212 of FIG. 2. Transceiver 310.b may be configured to communicate with the network 106 and the server 108, as discussed with respect to FIG. 1 regarding the UE 104. Although illustrated as separate transceivers 310.a and 310.b, these may be a single transceiver 310 that may communicate using a single communication protocol/hardware (e.g., BLE or NFC), or multiple protocols/hardware (e.g., LTE, 5G, BLE, NFC, etc.).

The UE 104 may receive monitored data via the transceiver 310.a (and in embodiments data entered by the user via the UE 104) and forward the data, or some subset thereof (e.g., stripped of patient information and/or encrypted where the tissue engineering device 102 did not do so) to the server 108 for back-end storage, data analysis, and/or access by one or more subscribing access devices 114.

Turning again to the compliance module 308, other examples of features include a calendar. The calendar may both maintain the treatment regimen prescribed by the treating physician, but also provide an interface to the patient using the tissue engineering device 102 that identifies various treatment details. For example, each day may be illustrated with an icon, showing for example a timeframe (e.g., a week, a month, etc.) with each day identifying whether treatment was compliant or not (e.g., a green dot for the day where compliant, red for non-compliant, and some shade scale of colors for partial compliance that is understandable with a legend). The calendar may also summarize treatment details, such as identifying a number of days compliant treatment has occurred, identifying how many days are left over the period of time for the course of the treatment, etc.

The calendar may further be used to organize pain scale and other information. Looking at pain scale data in particular, this may refer to a quantifiable pain scale that scales the amount of pain a user (of the tissue engineering device 102 as well as of the associated account profile that is accessible by the UE 104) is then feeling, whether in that moment or aggregated since the last periodic check. The scale may range, for example, between two numeric ends, such as zero and ten (or some other numbers, since this is exemplary only), with one end, such as zero, corresponding to no pain felt, to 10, a worst possible pain, with values in between scaling between the two. The interface may provide discrete value selections, e.g. via radio buttons or some other similar interface, while in other embodiments the interface may constitute a sliding scale that the user may manipulate via finger, mouse, or other input. The periodicity of the pain scale collection may be on a daily basis, or that otherwise coincides with the periodicity of the treatment itself (e.g., daily, every other day, etc.). Thus, with reference to the calendar described above with respect to the compliance module 308, the compliance module 308 may associate, and store, the collected pain scale information with the day on which the pain scale data was collected.

In addition to collecting pain scale information, the compliance module 308 may cause the UE 104 to collect images of the treatment of the patient (user). This may also be done on a periodic basis. This periodic basis may be the same as the periodic basis of the pain scale information prompts (that prompt the user to input the information). In such embodiments, after collecting the pain scale information the compliance module 308 may prompt (e.g., via an interface of the UE 104, or which may be sent to the tissue engineering device 102 as a prompt to an interface of that device to collect the response) to collect an image of the treatment site on the patient. In other embodiments, the compliance module 308 may prompt the user of the UE 104 to collect an image of the treatment site in response to the collected pain scale information exceeded a threshold. In that case, the compliance module 308 compares the pain scale information after it is collected to the threshold and determines whether to prompt the user to collect the image based on the result. When collected, the images may also be associated as the pain scale information with the calendar, and the compliance module 308 may store the collected image with the pain scale information under the day on which the pain scale data was collected.

The compliance module 308 may further collect information regarding activity level of the patient (i.e., the user of the UE 104). For example, the activity level may identify activities of daily living (or some other increment of time) as input from the patient. This may assume the form of a narrative that is sent with compliance information (e.g., as part of the compliance report discussed herein) that is coded by someone with access to the database in the server 108. As another example, this may assume the form of a pre-set field of possible options (e.g., a list of pre-selected activities of interest to the physician or the manufacturer of the tissue engineering device 102, or a list that may dynamically grow based on the user's selection of activities), with each selection providing some numeric value to assist in quantifying the activity level of the patient.

For example, for certain activities such as sports or jobs with specific physical activity requirements, activity above a threshold level (e.g., as quantified according to the concept described herein) may raise a flag that triggers notification of the physician that prescribed the treatment regimen. This may be, at least in part, because an increase in particular activity levels may be an indicator of future pain scale information increases. In response, the physician may review the activity, seek further information from the patient, send a message to the patient regarding risks of the activity, flag for subsequent scrutiny (e.g., because pain may increase later due at least in part to the activity), or take no action. In addition or alternatively, the compliance module 308 may collect information regarding compliance in taking one or more prescribed medications associated with the treatment regimen.

As another example of another feature for the module, the compliance module 308 may, during a particular periodic treatment, provide a status indicator that identifies how much time is remaining for the current treatment as the patient desires it. The compliance module 308 may further provide reminders to the patient via multiple alert approaches, including audible alerts, text alerts, email alerts, and visual alerts. For example, where the UE 104 is the patient's smartphone and the compliance module 308 is provided from an application downloaded from the server 108, then the alerts may be an alarm set to a particular time of day that the patient selected as the desired time to start treatment for that day per the regimen. The alarm may be audible and/or visual, as well as include a text or other notification that draws attention.

The compliance module 308 may dynamically modify the intensity of the alert (whether in terms of frequency of the alert, noticeability of the alert, or some combination thereof). This may be modified based on treatment data received from the tissue engineering device 102 over time. Thus, for example, where the patient is compliant with treatment over time, the reminders may be minimized to a system tray reminder without audible and/or other visual alerts. If, however, the compliance is below a threshold, the alerts may become more aggressive, with audible alerts, changing volume (e.g., higher volume as percent compliant goes down over time), intrusive visual displays (e.g., to disrupt text reading such as text reminders, interactive text-based messages, etc.), as well as potentially short audible reminders during phone use. The intensity of the reminders may increase as the level of compliance is determined to be decreasing over time, so as to encourage patient compliance with a treatment regimen designed for patient efficacy. In addition, an escalation hierarchy may be applied where, if the alerts are ignored by the patient/user of the UE 104 (e.g., by the compliance metric not changing, or not improving sufficiently, or the alerts are not acknowledged as being received, etc.), then the alerts may be escalated to additional parties. For example, escalation may be to a sales representative for the tissue engineering device 102 (and/or back-end services at the server 108), a customer service representative, a prescribing physician, a family member, and/or a health insurance provider (in an order of preference of escalation set either by the manufacturer, the prescribing physician, and/or the user/patient).

Further, where the treatment has already occurred for a given period of the treatment regimen, the compliance module 308 may dynamically reduce the reminders in either frequency or intensity, or both. For example, where on a given day the patient completes the treatment prior to a time for which reminders are scheduled, the compliance module 308 may cancel the reminder for that day. If, however, the time of day that the treatment occurs is important, the compliance module 308 may allow the alert to be, instead of a typical alert to treatment, a reminder that the time of day of treatment is important (where applicable) to the treatment in addition to the periodicity and duration. Where treatment is partially completed for the day when the reminder is scheduled, the reminder may be modified in its content and/or intensity to account for the amount of treatment already determined to be completed (e.g., from data already received from a paired tissue engineering device 102).

In addition to, or as an alternative to, the dynamic alerts, the compliance module 308 may modify alert preferences based on the patient interacting with settings of the compliance module 308, e.g. to activate the dynamic alerts, to set a static frequency/intensity of alerts over time, and/or further modify the alerts (whether dynamic or static) according to their preference and/or individual schedule. Further, the compliance module 308 may alert the patient audibly and/or visually when the treatment for the day is completed.

The compliance module 308 may further include an interface that the user of the UE 104 may use to trigger the UE 104 (via transceiver 310.*a* for example) to search for other tissue engineering devices 102 with which to pair. This may be applicable, for example, where a representative of either the manufacturer or the prescribing physician, etc. periodically seeks to visit the patient and obtain data from the tissue engineering device 102 during that visit (a so-called milk run). Thus, the compliance module 308 allows the UE 104 to pair with multiple tissue engineering devices 102, whether in sequence or in parallel.

The compliance module 308 may further include, such as in a management mode, useful information for the patient including an identified time/time of day prescribed for the PEMF treatment, a difference between the current time and the next prescribed treatment time, contact information for the prescribing physician and/or representative for the provider of the tissue engineering device 102, etc. Further, one or more links to online access systems, repositories, etc. may be provided. For example, a link may be provided to an online account system hosted by the server 110 of the manufacturer (or by the server 108) where the patient can update certain profile information. The compliance module 308 may further provide links to other patient treatment services as offered by the manufacturer and/or prescribing physician.

The compliance module 308 may direct the transceiver(s) 310 in receiving messages from one or more interested parties (e.g., prescribing physician, manufacturer, advertiser where patient has indicated willingness to accept such, etc.), displaying the messages locally via a display of the UE 104, and/or conveying the messages on to the tissue engineering device 102 with which the messages are associated. When in management mode, the interface may be further used (e.g., where the UE 104 is associated with a representative of the manufacturer or the physician) to modify one or more compliance thresholds used to trigger one or more alerts for the paired tissue engineering device(s) 102.

In some embodiments, the compliance module 308 causes the transceiver 310.b to transmit (either periodically or as they are received) the data (or some subset) from the tissue engineering device 102 (and/or from the user interface of the UE 104, such as pain scale information and/or treatment site images) to the server 108 for back-end storage, data analysis, and/or access by one or more subscribing access devices 114. The compliance module 308 may cause the data to be transmitted without further processing or by stripping additional identifying data (e.g., the data may be transmitted only with the device serial number of the associated tissue engineering device 102) and/or encrypting. Alternatively, the compliance module 308 may generate the compliance report (or some portion thereof) before transmitting to the server 108 (in which case the results may be displayed on the UE 104, for example). Moreover, in some examples the compliance report (or some portion thereof) may be generated by the tissue engineering device 102, transmitted to the UE 104 for display, and/or further transmitted to the server 108 (with stripping of relevant identifying data and/or encrypting as noted above) in similar manner. The compliance report, whether generated by the UE 104 or the server 108 (or the tissue engineering device 102), may include such things as a number of days that the patient has been compliant in using a tissue engineering device 102 according to a prescribed treatment regimen over time (whether since the last data was received or since some previous time point, such as the start of treatment).

The compliance report may further include a breakdown of the use of the tissue engineering device 102 on per-time frame basis (e.g., per day) to assist in identifying any trends of use (e.g., compliance dips during weekends, etc.). The compliance report may also include a percentage that identifies a total level of compliance to the prescribed treatment regimen—either a single percentage over the full duration, or on a more granular basis such as per week, per day, etc. Thus, compliance may be reported overall as well as for, or just for, each treatment day (e.g., depending on user or prescribing physician preference to name a few examples). As another example, the compliance report may include pain scale information collected from the user and stored per calendar collection times, and/or images of the treatment site. Thus, in embodiments of the present disclosure, tissue engineering device 102 use compliance, pain scale information associated with the use, and treatment site images may all be collected and available for use by physicians and other authorized representatives, e.g. either daily or some other periodic (i.e., aggregated or snapshot) basis. The compliance module 308, as part of generating the compliance report, may further analyze and characterize the data aggregated over time to identify likely amounts and types of activity sustained by the tissue engineering device 102 during the treatment regimen, and include this information in the compliance report.

The compliance report may further include information associated with patient recovery from compliance, including for example the pain scale data, activity levels according to a periodic metric, adherence to physical therapy protocols (e.g., including the tissue engineering device use, and/or other physical therapy protocols including exercises), and/or adherence to taking prescribed medications, to name just a few additional examples. Further, the compliance module 308 may include in the compliance report (or transmitted as part of the monitoring data to the server 108 for inclusion in a report there) additional analysis done on the monitoring data, including a determination using one or more embedded algorithms whether the patient is sedentary or mobile during each treatment session (based on the data from the tissue engineering device 102). This may be aggregated over time and analyzed by the UE 104 to determine further whether the patient is generally more or less mobile over a period of time (such as days, weeks, or months).

Where the compliance report is generated at the UE 104, e.g. by the compliance module 308 (such as via the processor 302), the UE 104 may strip the compliance report of patient information such as name, birthday, etc. prior to transmission to the server 108 so as to be compliant with any patient privacy laws in place (and/or by encrypting). A device identifier may still be included, which the server 108 may use to locate the patient assigned that device in a database.

Figure 4:
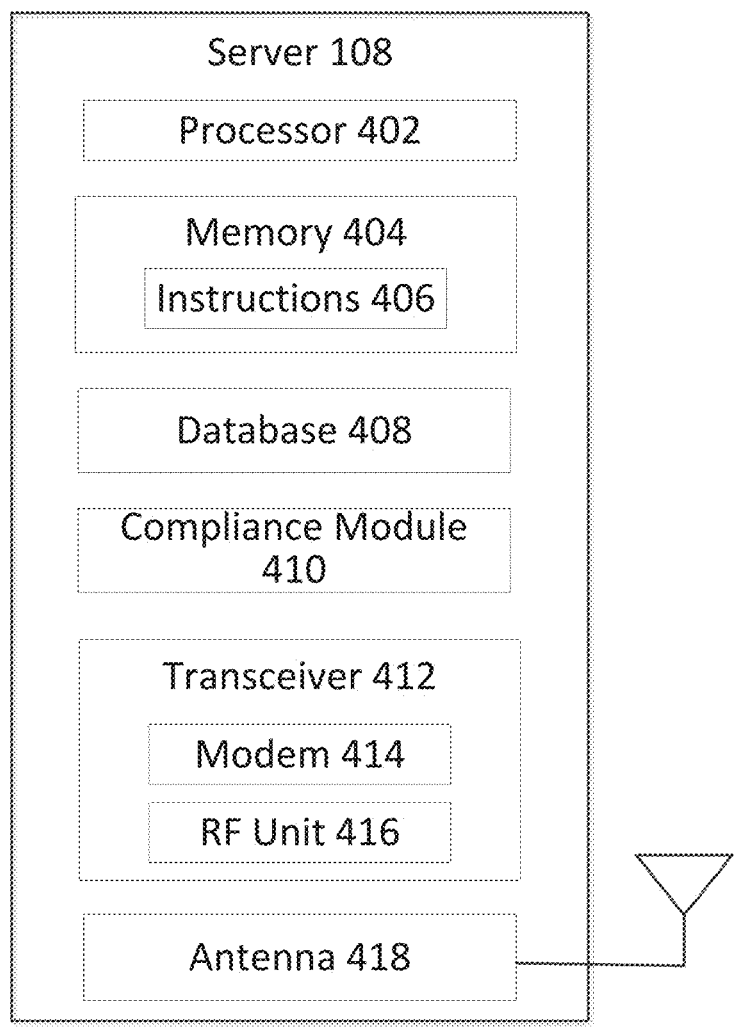
FIG. 4 is an organizational diagram of an exemplary server apparatus according to aspects of the present disclosure.

Turning now to FIG. 4, an organizational diagram 400 of an exemplary server apparatus (e.g., server 108) is illustrated according to aspects of the present disclosure. The server 108 may include a processor 402, a memory 404, a database 408, a compliance module 410, transceiver 412, and antennae 418. These elements may be in direct or indirect communication with each other, for example via one or more buses.

The processor 402 may have various features. For example, these may include a central processing unit (CPU), a digital signal processor (DSP), an application-specific integrated circuit (ASIC), a controller, a field programmable gate array (FPGA) device, another hardware device, a firmware device, or any combination thereof configured to perform the operations described herein with reference to the server 108 introduced in FIG. 1 above. The processor 402 may also be implemented as a combination of computing devices, e.g., a combination of a controller and a microprocessor, a plurality of microprocessors, one or more microprocessors in conjunction with a DSP core, or any other such configuration. For example, the processor 402 may be implemented as a plurality of processing cores.

The memory 404 may include a cache memory (e.g., a cache memory of the processor 302), RAM, MRAM, ROM, PROM, EPROM, EEPROM, flash memory, solid state memory device, hard disk drives, other forms of volatile and non-volatile memory, or a combination of different types of memory. In some embodiments, the memory 404 may include a non-transitory computer-readable medium. The memory 404 may store instructions 406. The instructions 406 may include instructions that, when executed by the processor 402, cause the processor 402 to perform operations described herein with reference to a server 108 in connection with embodiments of the present disclosure.

The server 108 includes the database 408 which stores data associated with a plurality of device profiles. Each device profile may be associated with a different tissue engineering device 102. Alternatively, each profile may be associated with a different physician, and therefore have multiple devices associated therewith, as just two examples. Each tissue engineering device 102 may be associated, in the database, with patients to which the devices have been prescribed. This association may be made by a representative, e.g. via the server 110, of either the manufacturer or the prescribing physician. The database 408 may further house treatment regimens, device profiles, patient profiles, physician profiles, manufacturer profiles, and/or sales representative profiles.

The database 408 may, upon receipt of treatment data from a UE 104 (or tissue engineering device 102 without relay by a UE 104) store the data into appropriate locations and associate the data in the database 408 with the appropriate profile(s). This data may include, as noted above, both information regarding compliance (such as number of days in compliant use, level of compliance per treatment) as well as pain scale and/or treatment site image data. The compliance module 410 may be used to manage the database 408, or alternatively another source of interaction. As treatment data is received, the compliance module 410 may cause the database 408 to be updated and the update acknowledged.

Over time, the compliance module 410 may aggregate the data received from one or more reporting tissue engineering devices 102 (whether collected periodically according to a schedule, in real time, or on demand to name some examples) and use this aggregated data to generate compliance reports, similar to as discussed above with respect to the compliance module 308 when generating compliance reports. The data forming the basis of the compliance reports may be obtained from the database 408 and/or from data as it is received from UEs 104/tissue engineering devices 102. Further, where the UE 104 generates compliance reports itself (via compliance module 308), these UE-generated compliance reports may be stored in the database 408 as well, and these UE-generated compliance reports may form the basis of longer-term trend compliance reports by the compliance module 410 of the server 108. The compliance module 410 may further analyze the monitoring data it receives to compare the patient's results to the results of similar patients' data. That similar data may be made available through other sources, such as public registers and/or other patient recorded outcomes.

The compliance module 410 may also generate the application that is downloaded by UEs 104 and becomes the compliance module 308 described above with respect to FIG. 3 when installed. Further, the compliance module 410 may cause the database 408 to store any messages received from a subscribing entity via an access device 114 (e.g., a representative of a physician) and the transceiver 412 to forward the message to the targeted tissue engineering device 102 (and/or paired UE 104).

As shown, the transceiver 412 may include the modem subsystem 414 and the radio frequency (RF) unit 416. The transceiver 212 can be configured to communicate bi-directionally with other devices, such as UEs 104 and/or other network elements such as those in the wireless network 106. The modem subsystem 414 may be configured to modulate and/or encode data according to any of a variety of coding schemes. The RF unit 416 may be configured to process (e.g., perform analog to digital conversion or digital to analog conversion, etc.) modulated/encoded data from the modem subsystem 414 (on outbound transmissions) or of transmissions originating from another source. Although shown as integrated together in transceiver 412, the modem subsystem 414 and the RF unit 416 may be separate devices that are coupled together to enable the server 108 to communicate with other devices. Although FIG. 4 illustrates antenna 418 as a single antenna, antenna 418 may include multiple antennas of similar or different designs in order to sustain multiple transmission links.

Figure 5:
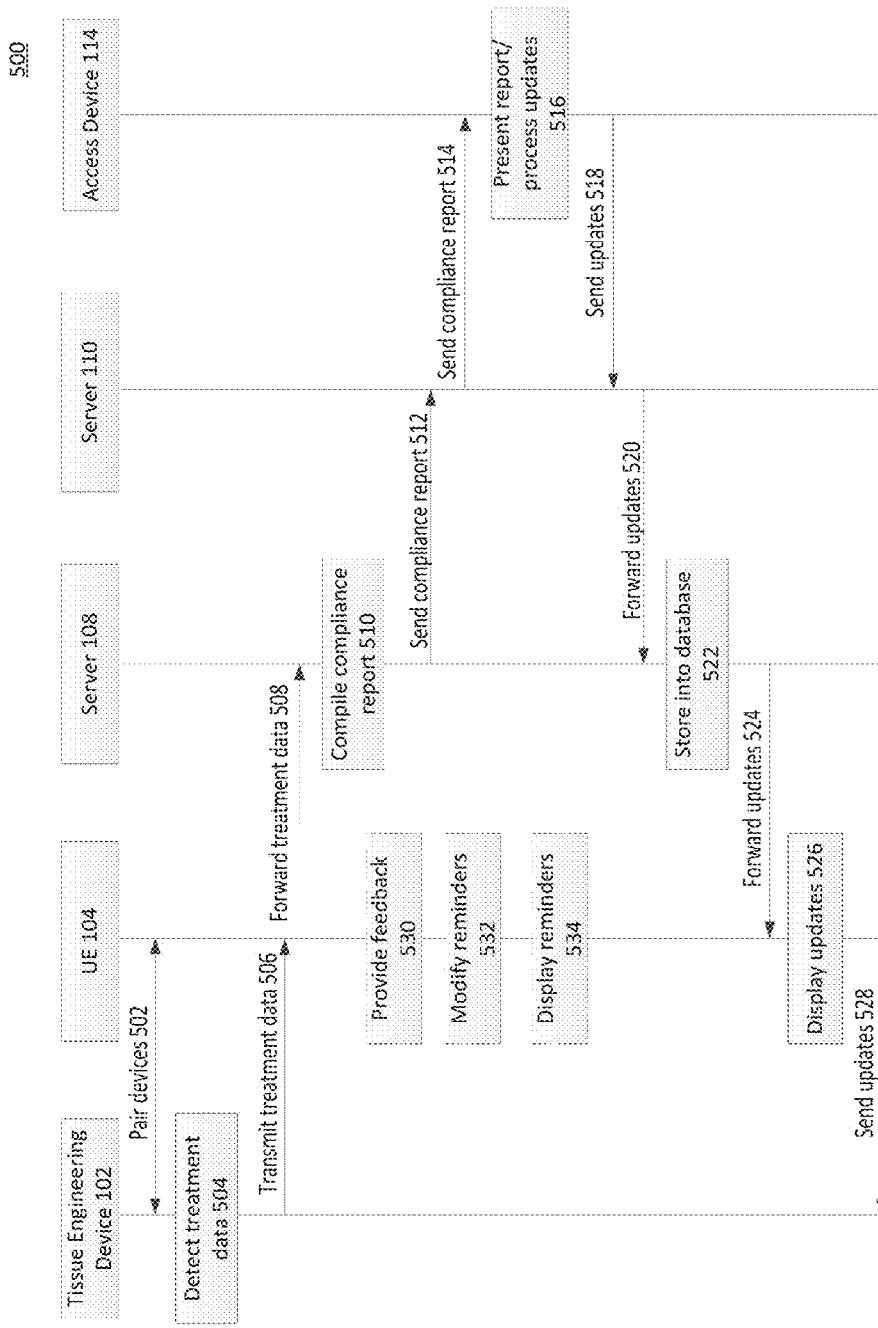
FIG. 5 is a protocol diagram illustrating exemplary aspects between treatment and monitoring system elements according to aspects of the present disclosure.

These different devices cooperate to provide an exemplary treatment and monitoring system. FIG. 5 is a protocol diagram 500 illustrating exemplary aspects between treatment and monitoring system elements according to aspects of the present disclosure. As illustrated, the protocol diagram 500 shows exemplary interactions between a tissue engineering device 102 (exemplary of potentially multiple such devices), a UE 104 (exemplary of potentially multiple), server 108 (exemplary of potentially multiple), server 110 (exemplary of potentially multiple), and an access device 114 (exemplary of potentially multiple).

At action 502, a UE 104 pairs with a tissue engineering device 102. This may occur, for example, via BLE or NFC connections as just some examples. This may occur periodically as the devices come within range of each other. Further, where the devices remain in range with each other outside of necessary times of communication (e.g., no treatment is scheduled at a particular time where the devices are in sufficient proximity to each other, etc.), the devices may only pair at action 502 as determined necessary so as to conserve energy (though the devices may alternatively remained paired so long as they are in proximity to each other).

At action 504, the tissue engineering device 102 detects treatment data. This may include sensor data from the one or more sensors (such as patient proximity data, accelerometer data, gyroscope data, etc.). This may also or alternatively include detecting when treatment is not occurring though it should according to a prescribed treatment regime. Although illustrated as occurring after the pairing at action 502, the data from action 504 may have been detected previously and stored until pairing occurred.

At action 506, the tissue engineering device 102 transmits the treatment data to the UE 104. In embodiments where the tissue engineering device 102 is capable of communicating with the server 108 without the relay assistance of a paired UE 104, this may not occur. Further, where the transceiver is included with a power supply or otherwise, this may include transmitting the treatment data to the power supply, from which the treatment data will be transmitted once it is paired with a UE 104. However transmitted, the tissue engineering device 102 may transmit the data with patient identifying information stripped from the data, so that only the data with a device identifier are included, and/or by encrypting the data.

At action 508, the UE 104 receives the treatment data transmitted from the tissue engineering device 102 and forwards it to the server 108, for example via one or more networks 106. Where the tissue engineering device 102 failed to strip (and/or encrypt) sufficient data to ensure compliance with any patient privacy laws, then the UE 104 may further strip (and/or encrypt) the data before transmission to the server 108. In some embodiments, the UE 104 may prompt the user of the UE 104 (e.g., via the compliance module 308) for pain scale information coincident with the treatment occurring with the tissue engineering device 102 (e.g., daily). In other embodiments, the UE 104 may prompt the user when it is paired with the tissue engineering device 102, regardless of whether that is coincident in time with when treatment is occurring. In yet other embodiments, the UE 104 may prompt the user on a scheduled basis regardless of whether treatment has occurred on that day yet or not (e.g., daily).

Yet further, the UE 104 may occasionally or periodically prompt the user of the UE 104 (e.g., via the compliance module 308) to collect an image of the treatment site (such as via a camera integrated with, or paired with, the UE 104; alternatively, the image may be collected by any camera and associated with the user's profile at either the UE 104 or the server 108). The images may be collected at the same periodic rate at which the pain scale information is collected (e.g., daily) or only in response to the reported pain exceeding a threshold on the pain scale. This information is all described in association with action 508 of FIG. 5 for simplicity of discussion, though it may be collected at times unrelated to the receipt of treatment data from action 506 (e.g., on a scheduled basis that may be consistent with the treatment regimen periodicity but independent of the actual time selected by the user for treatment on any given day).

At action 510, the server 108 compiles a compliance report for the patient associated with the tissue engineering device 102 based on the most recently received data from action 508. As part of this process, the server 108 may re-associate the data from the tissue engineering device 102 to the patient to which the device was prescribed, for example by looking up the device identifier of the tissue engineering device 102 included in the data with the records in the database 408 (FIG. 4).

At action 512, after the compliance report is generated (either by the server 108 or supplemented by the server 108 after generation at the UE 104 where applicable), the server 108 sends, or makes available, the compliance report to other entities. This may be in a periodic transmission, or rendering the compliance report available for access on demand by authorized parties. As illustrated, the server 108 sends the compliance report to the server 110 (e.g., that hosts an access portal for accessing parties such as a representative for the device manufacturer and the prescribing physician). The server 110 may then make the compliance report available to the appropriate parties.

For example, the server 110 may maintain different sets of permissions (although discussed with respect to server 110, this may alternatively be maintained by the server 108 e.g. as part of the database 408) for different accessing parties. For example, a representative of the manufacturer may only have access to the compliance data (and/or pain management data) without identifying the patient, while the prescribing physician may have access to the identity of the patient as well.

The server 110, at action 514, sends the compliance report (or some subset thereof, depending upon permission level) to an access device 114, such as that of a representative of a physician or a manufacturer of the tissue engineering device 102.

At action 516, the compliance report (whatever portion allowed) is presented via the access device 114 and any updates are processed at that time. For example, the pain treatment data may be accessed via the access device 114 (where presented/available) on a calendar basis, such as via a snapshot listing for multiple days in a row. If the reviewing entity determines that the pain scale information is noteworthy, the reviewing entity may select the day associated with that information and access one or more images of the treatment site associated with that same day (e.g., to look for redness or other signs of infection or other condition). As another example, the prescribing physician may desire to send a message to the patient (such as encouragement to increase compliance, to indicate a reminder for a follow-up appointment, to change the regimen, follow-up regarding pain information, etc.).

At action 518, the access device 114 sends the message/update back to the server 110 (e.g., by entry into a field via a portal provided by the server 110).

The server 110, in turn, at action 520 forwards the message/update to the server 108.

At action 522, the server 108 may store the message/update into the database 408. For example, where the physician desires to change the treatment regimen, this may be stored in the appropriate database location associated with the patient and tissue engineering device 102, so that future compliance reports may accurately reflect the most recent treatment regimen information.

At action 524, the server 108 forwards the message/update to the UE 104 (where the UE 104 acts as a relay to the tissue engineering device 102 to which the message/update is intended).

At action 526, the message/update may be displayed by the UE 104. Thus, if it is an update that does not necessarily need to be displayed, the UE 104 may still display to notify the patient, and messages intended for the UE 104 to display may similarly be displayed.

At action 528, any updates (e.g., to treatment regimen) are forwarded from the UE 104 to the tissue engineering device 102 (or from the server 108 to the tissue engineering device 102 where a UE 104 is not required/used for relaying data).

Action 530 may occur throughout the actions 504 through 528. At action 530, feedback for the current periodic application of the treatment is provided. This may include the treatment data transmitted at action 506. Further, this may include providing treatment feedback dynamically to the user as treatment is occurring, either via a display on the tissue engineering device 102 and/or a display on the UE 104 paired or associated with the tissue engineering device 102.

At action 532, any reminders scheduled or provided by default, for example by the compliance module 308 of UE 104, may be modified based on the feedback received at action 530. Thus, a reminder for treatment may be modified (e.g., either in intensity such as sound or visual, or in content) to take into account a level of treatment already reached for the current periodic application according to the treatment regimen.

At action 534, the reminder (and, if applicable, as modified from action 532) is displayed to the intended displays, whether a display of the UE 104, a display of the tissue engineering device 102, and/or any other devices to which a reminder is sent or scheduled.

This process may repeat over time as data is periodically reported from the tissue engineering device 102 for compliance monitoring and reporting, so that treatment by the tissue engineering device 102 may be improved in efficacy and thereby reduced treatment times that better align with proven outcomes.

Figure 6:
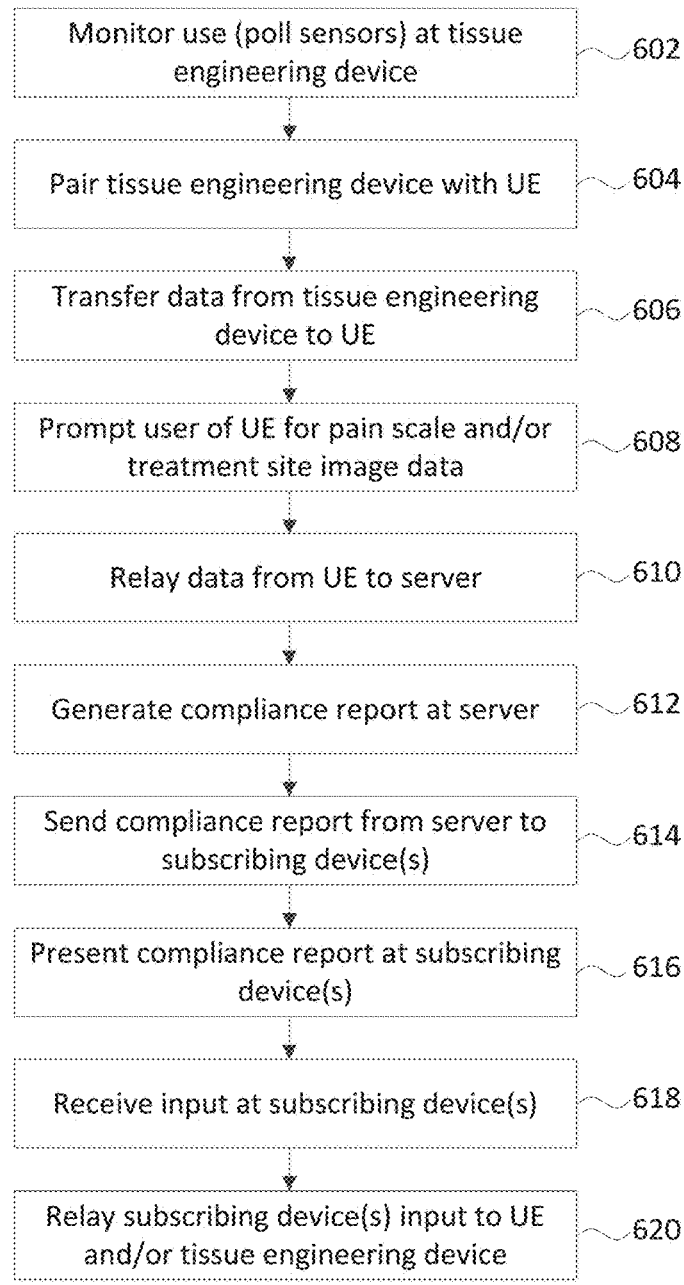
FIG. 6 is a flowchart illustrating an exemplary method for tissue treatment and monitoring according to aspects of the present disclosure.

FIG. 6 illustrates a flowchart illustrating an exemplary method 600 for tissue treatment and monitoring according to aspects of the present disclosure. In particular, the method 600 illustrates the operation of the system including the tissue engineering device 102, UE 104, server 108, server 110, and access device 114 according to embodiments of the present disclosure. For simplicity of discussion, reference is made to the devices in the singular, though embodiments of the present disclosure support the interaction of multiple devices within the system in similar manner. It is understood that additional steps can be provided before, during, and after the steps of method 600, and that some of the steps described can be replaced or eliminated from the method 600.

At block 602, the tissue engineering device 102 monitors use (or nonuse) of the tissue engineering device 102. This may occur, for example, by periodically polling one or more sensors associated with the tissue engineering device 102 as discussed above with respect to FIG. 2 and also FIG. 7A below. Thus, for example, at times the result of the monitoring may identify that the tissue engineering device 102 is not in use, while at other times the determination is that it is in use. Block 602 may occur throughout the aspects discussed below (e.g., pairing devices, transferring data, receiving data, etc.). Further, the tissue engineering device 102 may display an overall treatment compliance indication at the tissue engineering device 102 (in addition to the information passed on to the UE 104/server 108), such as a percentage compliant over time.

At block 604, the tissue engineering device 102 pairs with a UE 104. This may be a UE 104 of the patient with which the tissue engineering device 102 is also associated, and/or a UE 104 of another entity, such as a representative of the manufacturer or the prescribing physician, that is visiting the patient (or that the patient is visiting). The pairing may occur automatically, e.g. with the UE 104 being previously associated, or may be manually performed.

At block 606, the tissue engineering device 102 transfers monitoring data to the UE 104. The transfer may strip identifying data of the patient to comply with privacy requirements (and/or encrypt the data). This may be a real-time transfer of monitoring data as it is obtained, of monitoring data obtained over a prior period (e.g., either a set time frame or since a previous pairing), or some combination of both. For example, to conserve on power, the monitoring data may be transferred according to a schedule, e.g. once a day, and no further transfers are done automatically unless otherwise initiated manually by a user (e.g., by bringing an application in the paired UE 104 from a background process to an active, foreground process and requesting a data update) apart from essential communications such as regard error messages, battery status information, etc. as needed.

At block 608, the UE 104 prompts a user of the UE 104 to input pain scale information with respect to the site of treatment (for example). The user may input the pain scale information via an interface of the UE 104 as discussed with respect to the embodiments above. Moreover, the UE 104 may prompt the user to also collect an image of the treatment site, whether on a periodic basis or in response to the pain scale information response exceeding a threshold (e.g., to make data available to assist a physician in determining whether an infection or other problem is occurring at the treatment site). This information may be collected at the same periodicity as the use of the tissue engineering device 102 specified in the treatment regimen. Thus, additional analysis may be performed by the UE 104 to discover broader trends for the patient, such as identifying whether the patient is more sedentary or mobile during each treatment session. The information, including level of mobility, may be aggregated over a longer time duration.

At block 610, the UE 104 relays the monitoring data it receives to a server 108 and, where obtained, the pain scale information and/or image(s) collected of the treatment site, (and, where available, additional analysis performed by the UE such as the level of mobility to name just an example) by first further stripping the data (and/or encrypting) of any patient identifying data if further needed or not done previously, so as to comply with any privacy requirements for the patient while transmitting over a network 106 and storing at a server 108. Similar to the communication between the tissue engineering device 102 and the UE 104, the UE 104 may relay the monitoring data to the server 108 in real time or according to a schedule, e.g. once a day, unless otherwise initiated manually by a user (e.g., by bringing an application in the UE 104 from a background process to an active, foreground process and requesting a data update) apart from essential communications as needed. The monitoring data (referred to generally here to include both the data collected by the tissue engineering device 102 and the pain/image data collected by the UE 104) may be relayed by one or more networks 106 to which the UE 106 is in communication and which can reach the server 108.

At block 612, the server 108 which received the relayed monitoring data from the UE 104 generates a compliance report based on the relayed monitoring data. As part of this process, the server 108 may first re-associate the tissue engineering device 102 for which the monitoring data was sent to the appropriate patient in a database maintained by the server 108. Therefore, the report may further be based on data stored previously about the particular patient/tissue engineering device 102.

As part of generating the compliance reports at block 612, the server 108 may further generate various permissions for the generated compliance report—these permissions may allow greater or reduced access to information in the reports, such that one level of permissions may limit the accessing entity from viewing any patient identifying information, while another level of permissions may allow the accessing entity to view the patient identifying information as well. Where the compliance report was generated by the UE 104 or tissue engineering device 102 already, and conveyed to the server 108, block 612 may include the generation of permissions as discussed. Further, at the server 108 additional compliance information may be generated such as by comparing results from the patient's data to results of similar patients' data made available through other sources, such as public registers or other reported outcomes.

At block 614, the server 108 sends the compliance report to one or more subscribing devices, identified as the access devices 114 in FIG. 1. Where different levels of permissions are included, the server 108 may send the compliance report (or make available at the server 108, with the sending the compliance report being a message notifying the recipient of availability of the report to be accessed) with the permission level included to the various access devices 114. In some embodiments, the compliance report may be modified at the server 108 according to the level of permission of the target recipient, and then sent, while in other embodiments the compliance report may be broadcast and each access device 114 may only be able to access based on a level of permission stored at the access device 114.

At block 616, the subscribing access device(s) 114 that received the compliance report from the server 108 may present the compliance report, or some portion thereof, to a user of the access device 114. For example, the user may be a representative of the prescribing physician for the tissue engineering device 102, looking to monitor a level of compliance with the prescribed treatment regimen and/or pain management. With respect to pain management, this may include a prediction of future pain scale increases based on an amount of activity identified by the user (e.g., playing a sport during the treatment regimen, a physically demanding job, etc.) based on an increase of physical activity now. As another example, the user may be a party related to the patient, such as a spouse, parent, or child, etc.

At block 618, the access device 114 that received the compliance report at block 616 receives input, if any, from a user of the access device 114 via one or more inputs such as text, voice, and video. The input may include a simple acknowledgment of receipt of the compliance report, a message intended for the patient using the tissue engineering device 102, a change in treatment regimen input by the prescribing physician, and/or a reminder about compliance.

At block 620, the access device 114 that received the input at block 618 relays the input to the patient of the tissue engineering device 102, for example by forwarding the input to the server 110 (where included), server 108, via network 106, and to the UE 104 for display there and/or forwarding on to the tissue engineering device 102.

The actions described above with respect to FIG. 6 may continue over multiple periodic applications (e.g., where a periodic application occurs once a day for a specified number of hours, the above may occur over multiple days/weeks/months as treatment should continue according to the prescribed treatment regimen).

Figures 7A, 7B:
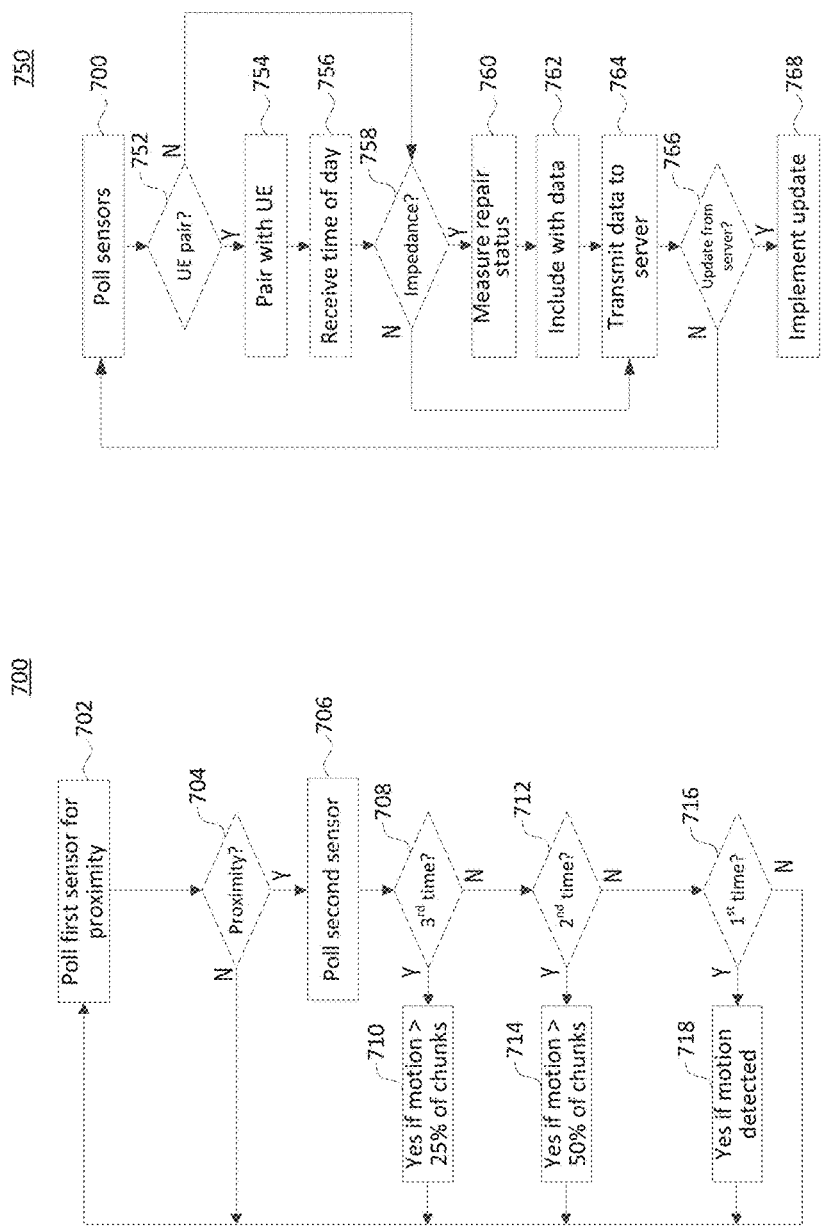
FIG. 7A is a flowchart illustrating an exemplary method for tissue treatment device sensor polling according to aspects of the present disclosure.
FIG. 7B is a flowchart illustrating an exemplary method for tissue treatment device compliance monitoring according to aspects of the present disclosure.

Turning now to FIG. 7A, a flowchart illustrating an exemplary method 700 for tissue treatment device sensor polling is provided according to aspects of the present disclosure. In particular, the method 700 illustrates aspects of operation of the tissue engineering device 102 according to embodiments of the present disclosure. It is understood that additional steps can be provided before, during, and after the steps of method 700, and that some of the steps described can be replaced or eliminated from the method 700.

At block 702, a processor of the tissue engineering device 102 polls a first sensor to identify whether some tissue of the patient is within a threshold proximity of the first sensor (and, therefore, within a threshold proximity of the tissue engineering device 102). For example, the first sensor may be an infrared sensor and/or a capacitive sensor that is polled periodically.

At decision block 704, if the information from the first sensor as a result of the poll at block 702 indicates that the tissue engineering device 102 is not within the threshold proximity to the patient, then the method 700 returns to block 702 to poll again until it is determined that the tissue engineering device 102 is within the threshold proximity to the tissue of the patient.

If, at decision block 704, it is determined (e.g., by processor 202 of the tissue engineering device 102) that the tissue engineering device is within the threshold proximity of the tissue of the patient, then the method 700 proceeds to block 706.

At block 706, the processor of the tissue engineering device 102 polls a second sensor. For example, the second sensor may be used to identify whether the tissue engineering device 102 is actually in use by the patient, such as to skirt attempts to dupe a sensor (e.g., the patient placing the tissue engineering device 102 on a running washing machine that generates a false positive where one of the sensors is an accelerometer, etc.). As an example, the second sensor may be an accelerometer (and/or a gyroscope, either operating in cooperation with the accelerometer or in place of the accelerometer).

The method 700 proceeds to decision block 708. The method 700 may include multiple polling periods. A first polling period may be short, such as every 100 ms. A second polling period may be longer than the first polling period, such that multiple first polling periods may occur during a second polling period. For example, the second polling period may have a duration of 3 seconds or 30 seconds. A third polling period may be longer than the first and second polling periods, such that multiple first and second polling periods may occur during a third polling period. For example, the third polling period may have a duration of 30 seconds, multiple minutes, or multiple tens of minutes. The numbers given herein are exemplary only. Further, the number of polling periods is exemplary—more or fewer may be included according to embodiments of the present disclosure.

At decision block 708, if a third polling period time has not yet elapsed, then the method 700 proceeds to decision block 712.

At decision block 712, if a second polling period (i.e., a polling period shorter than the third polling period but longer than the first polling period) time has not yet elapsed, then the method 700 proceeds to decision block 716.

At decision block 716, if a first polling period (i.e. a polling period shorter than the other polling periods) time has not elapsed, then the method 700 returns to block 702 for further polling. Otherwise, the method 700 proceeds to block 718.

At block 718, if any motion has been detected by the second sensor (as identified from the poll at block 706), then the processor 202 records a "yes" for the first polling period. This indicates that motion has been detected by the second sensor during the first polling period. Otherwise, if no motion is detected during the first polling period then a "no" is recorded. The method 700 then proceeds back to block 702 as laid out above.

Returning to decision block 712, if the second polling period time has elapsed (therefore meaning that multiple first polling periods have occurred, each with respective "yes" or "no" results recorded), then the method 700 proceeds to block 714.

At block 714, the processor 202 determines whether motion has been detected more than 50% of the chunks of time (referring to each polling period as a "chunk of time"; in this example, more than 50% of the first polling periods that occur within a second polling period). Thus, the processor 202 may determine whether more than 50% of the first polling periods within the second polling period have a "yes" associated therewith. The value of 50% is exemplary in association with the second polling period. The percentage may be greater or less than this value, so long as it is greater than a percentage value associated with the third polling period as discussed further below. If more than 50% of the first polling periods have a "yes" recorded therewith, then the processor 202 records a "yes" for the second polling period. The method 700 then proceeds back to block 702 as laid out above.

Returning to decision block 708, if the third polling period time has elapsed (therefore meaning that multiple first and second polling periods have occurred, each with respective "yes" or "no" results recorded), then the method 700 proceeds to block 710.

At block 710, the processor 202 determines whether motion has been detected more than 25% of chunks of time (in this example, more than 25% of the second polling periods that occur within a third polling period—alternatively, this may also look at the first polling periods that occur within the third polling period). Thus, the processor 202 may determine whether more than 25% of the second polling periods within the third polling period have a "yes" associated therewith. The value of 25% is exemplary in association with the third polling period. The percentage may be greater or less than this value, so long as it is less than the percentage value associated with the second polling period. If more than 25% of the second polling periods have a "yes" recorded therewith, then the method 700 records a "yes" for the third polling period. The method 700 then proceeds back to block 702 as laid out above.

The "yes" values recorded for the third polling periods may be interpreted to mean that the tissue engineering device 102 has been used in proximity to the tissue of the patient during the course of the third polling period of time. The data provided to the UE 104 when paired with the tissue engineering device 102 may include the results from the third polling period only, or some or all of the polling periods for further refining where compliance reports are generated, for example as discussed with respect to FIG. 7B.

FIG. 7B is a flowchart illustrating an exemplary method 750 for tissue treatment device compliance monitoring according to aspects of the present disclosure. In particular, the method 750 illustrates additional aspects of operation of the tissue engineering device 102 according to embodiments of the present disclosure. It is understood that additional steps can be provided before, during, and after the steps of method 750, and that some of the steps described can be replaced or eliminated from the method 750.

At block 700, one or more sensors are polled by a processor of the tissue engineering device 102. For example, the first and second sensors discussed with respect to FIG. 7A above are polled according to the method 700 discussed above. As a further example, other sensors may also be polled, such as an impedance monitor sensor (e.g., to identify healing progression of specific musculoskeletal tissues) and/or a GPS sensor. For purposes of this discussion, an impedance monitor will be described.

At decision block 752, if the tissue engineering device 102 detects a pairable UE 104 (e.g., via a BLE connection or other type of wired and/or wireless connection), then the method 750 proceeds to block 754.

At block 754, the tissue engineering device 102 pairs with the UE 104 detected at decision block 752. This pairing may occur according to the wired and/or wireless connection identified at decision block 752.

At block 756, the tissue engineering device 102 may receive a time of day from the UE 104 paired at block 754. This is illustrated with dashed lines to indicate the optionality of this feature. This may be useful where the tissue engineering device 102 is first being used and paired with a UE 104, so that the time at the tissue engineering device 102 may be set to correspond to the time zone and/or time of the paired UE 104 (for example, where the UE 104 obtains its time from a network 106). This may be further useful in situations where the tissue engineering device 102 is transported to a different time zone, so that reminders may be coordinated with the UE 104.

Whether or not block 756 occurs, at decision block 758 if an impedance monitor sensor is included and operating, then the method proceeds to block 760. Returning to decision block 752, if the tissue engineering device 102 does not detect a pairable UE 104, then the method 750 proceeds to decision block 758.

At block 760, the data obtained from the impedance monitor sensor are used to measure a repair status of the monitored tissue. For example, impedance spectroscopy may be used to identify different types of tissue of the patient and correlate that to the known types of tissues present in the different stages of healing. Based on this correlation, an estimate of the progress of healing may be made.

At block 762, the tissue engineering device 102 may include the measured repair status from block 760 with the other monitoring data (e.g., the data provided from method 700) that is transmitted to the UE 104 for generation (at the UE 104 and/or the server 108) of compliance reports and otherwise banking in one or more databases.

At block 764, the measured repair status data is transmitted to the server 108, whether relayed via the UE 104 or otherwise sent to the server 108. This may be transmitted with the other data, such as when included at block 762, or sent independently therefrom.

Returning to decision block 758, where no impedance monitor is included (or it is not operating), then the method 750 proceeds to block 764. In situations where the method 750 reached decision block 758 because the tissue engineering device 102 is not paired with a UE 104, the data may be transmitted at block 764 as noted above where a UE 104 is not required to relay. If, however, a relay is required, the method 750 may enter a delay pattern until a UE 104 is detected and pairing occurs and/or more data from the sensors are polled. Further, where the relay further (or alternatively) includes pairing with a transceiver in a coupled accessory (e.g., power supply or docking station), whether to communicate with UE 104 or network 106, a delay pattern may be entered until the connection to the transceiver is made, and thereafter until a UE 104 is detected and pairing occurs. As noted above, in some embodiments the tissue engineering device 102 transmits data that it collects without further analysis, while in other embodiments the tissue engineering device 102 may display an overall treatment compliance indication at the tissue engineering device 102 (in addition to the information passed on to the UE 104/server 108), such as a percentage compliant over time.

From block 764, the method 750 proceeds to decision block 766. At decision block 766, if any update has been received from the server 108 (whether relayed by UE 104 or not), then the method 750 proceeds to block 768. The update may be, for example, a change in the prescribed treatment regime (e.g., based on the prescribing physician reviewing a compliance report that may include both compliance and impedance monitor data) made via an access device 114 and routed through the server 108 (and server 110, where applicable).

At block 768, the update is implemented by the tissue engineering device 102 (for example, storing the update in local memory to implement in terms of reminders of the schedule, treatment parameters when treatment occurs, etc.). The method 750 returns to block 700 to continue polling sensors.

Returning to decision block 766, if no update is received, then the method 750 returns to block 700 to continue polling sensors.

Figure 8:
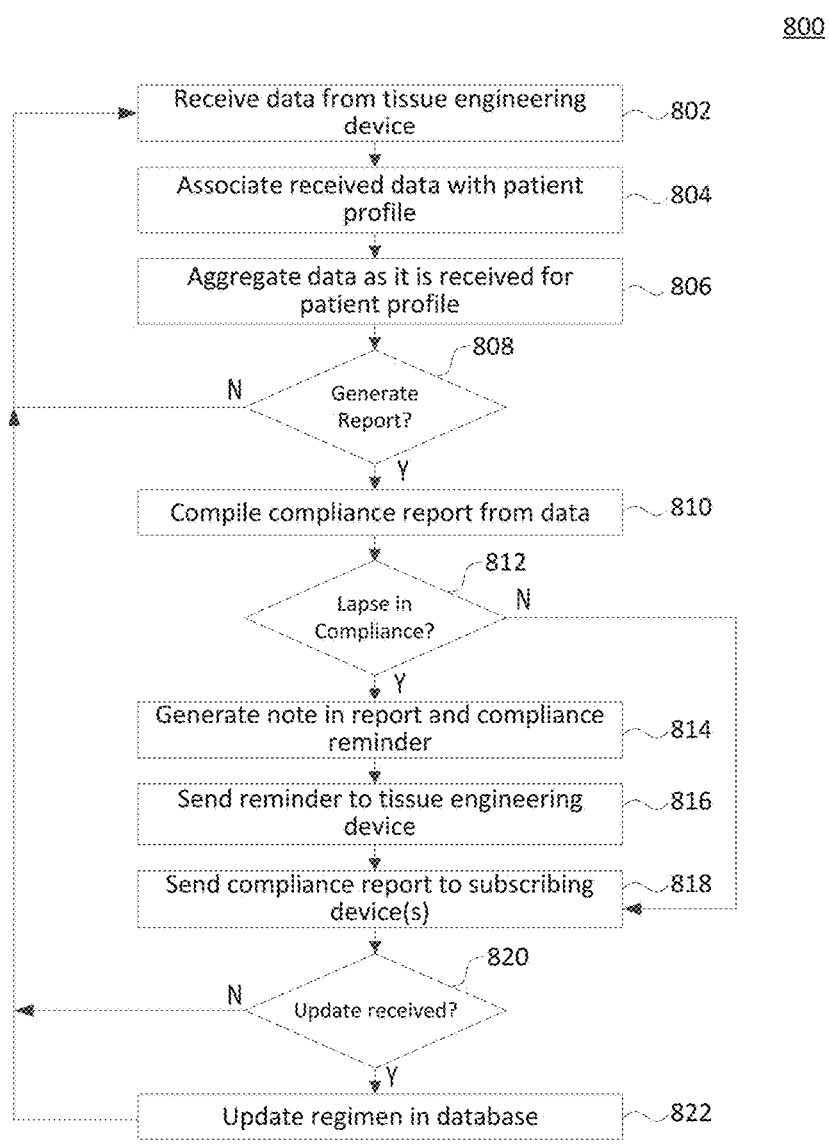
FIG. 8 is a flowchart illustrating an exemplary method for tissue treatment device compliance monitoring according to aspects of the present disclosure.

Turning now to FIG. 8, a flowchart illustrating an exemplary method 800 for tissue treatment device compliance monitoring is provided according to aspects of the present disclosure. In particular, the method 800 illustrates aspects of operation of the server 108 according to embodiments of the present disclosure. For simplicity of discussion, description will be made with respect to a single tissue engineering device 102 in communication with the server 108 via a network 106 and UE 104, though it is understood that the server 108 may be in communication with any number of tissue engineering devices 102 via any number of UEs 104 and networks 106. It is understood that additional steps can be provided before, during, and after the steps of method 800, and that some of the steps described can be replaced or eliminated from the method 800.

At block 802, the server 108 receives data from a tissue engineering device 102. This data may include compliance information over a prior time period (e.g., the third polling period described in FIG. 7A and/or the other polling periods) and/or impedance monitoring data. The data may be received at block 802 from the tissue engineering device 102 via a relaying UE 104 paired with the tissue engineering device 102, or where the relaying UE 104 is not required from network 106 (or, under either approach, from a connected accessory (e.g., power supply or docking station as just some examples). Moreover, pain scale information may be received from UE 104 and/or image data of the treatment site, as collected by the UE 104. Thus, the data the server 108 receives from block 802 may be from both the tissue engineering device 102 and the UE 104, or all from the UE 104 where the UE 104 serves as a relay for the tissue engineering device 102. The data may be received without any analysis having been performed yet, or with some analysis at the tissue engineering device 102 (e.g., overall compliance such as percentage compliant), the UE 104 (e.g., additional trend analysis to discover broader trends including a mobility level of the patient), or a combination of both. In some embodiments, the data is received with any patient identifying information stripped (and/or with the data encrypted). The data may instead identify nothing more than the tissue engineering device 102 itself (e.g., serial number or other identifier).

At block 804, where patient identifying information has been stripped (e.g., to comply with privacy requirements where applicable), the server 108 associates the received data with an appropriate patient profile maintained in a database 408 of the server 108. For example, the database 408 may store the device identifiers in association with the patients to which those tissue engineering devices 102 have been prescribed and provided. Thus, the server 108 may look up the identifier of the tissue engineering device 102 to identify the patient to which it has been provided. Where the data was encrypted, the server 108 decrypts the data (whether with the information stripped or not).

At block 806, the server 108 aggregates data for the tissue engineering device 102 as it is received (whether that is periodically, real time, on demand, etc.), and stores the data with the patient profile identified from block 804.

At decision block 808, if it is determined that it is not time to generate a compliance report (e.g., the prescribing physician has set a report generation period, such as weekly/monthly/some other time frame and/or the manufacturer has set a default report generation period), then the method 800 returns to block 802.

If, instead, it is time to generate a compliance report, then the method 800 proceeds to block 810. At block 810, the server 108 generates a compliance report based on the data received in the previous steps. This may occur whether or not the UE 104 also generates a compliance report (and/or whether or not the tissue engineering device 102 did an initial analysis to display an overall compliance at the tissue engineering device 102)—for example, where the UE 104 also generates a compliance report, the server 108's generation of a compliance report may involve including patient identifying information to the compliance report, including access permissions to the compliance report, comparing patent data results with similar patients' data from other sources, and/or generating a new compliance report that aggregates multiple shorter-term compliance reports from the UE 104 based on aggregated data in the database 408 over a set period of time.

With the compliance report generated at block 810, the method 800 proceeds to decision block 812. At decision block 812, the server 108 may automatically determine based on the generated compliance report whether a lapse in compliance has occurred. This may be done by comparing the content of the compliance report against a threshold compliance amount (e.g., a threshold compliance percentage, a threshold number of compliant days, and/or a threshold number of compliant treatment periodic applications to name some examples). If below the threshold, then the method 800 may proceed to block 814.

At block 814, the server 108 generates a note that may be included in the compliance report that identifies the failure in compliance for further review, and/or may generate a compliance reminder for the patient.

At block 816, the server 108 may send the reminder where generated to the tissue engineering device 102. This reminder may be expressly targeted to a UE 104 that is associated with the patient that is supposed to use the tissue engineering device 102, as well as (or alternatively) to the tissue engineering device 102 itself for its display. The reminder may be further sent to other interested, subscribed (or otherwise associated) parties to the patient, such as spouses, parents, children, etc.

At block 818, the server 108 sends the compliance report generated at block 810 to access device(s) 114 that have been subscribed for the particular patient. For example, the access devices 114 may include devices associated with the patient, with relatives of the patient, friends of the patient, the prescribing physician, and/or a representative of the manufacturer of the tissue engineering device 102 (or provider of the server 108 or server 110).

Where the generation of the compliance report included permissions, the compliance report at block 818 may be provided to the different access devices 114 according to their respective permission levels. Although described as being provided to the access devices 114 (e.g., pushed to those devices), this may alternatively describe the compliance report being made available via a portal (such as provided by server 110) for access by the access devices 114 on demand, or some combination thereof.

Returning to decision block 812, if no lapse in compliance has been automatically detected, then the method 800 may proceed to block 818 as discussed above, and proceed from there to decision block 820.

At decision block 820, if any update has been received from an access device 114 (e.g., from the prescribing physician), then the method 800 proceeds to block 822. The update may be, for example, a change in the prescribed treatment regime (e.g., based on the prescribing physician reviewing a compliance report that may include compliance and impedance monitor data, pain scale information, and/or treatment site image(s), or some sub-combination thereof) made via an access device 114 (and optionally routed through server 110).

At block 822, the server 108 updates the treatment regimen in its database 408 according to the update received as determined at decision block 820. This is useful so that future compliance reports reflect updated and accurate information. The server 108 also sends the update to the tissue engineering device 102 (whether relayed via a UE 104 or not). Where the update is (or includes) a message for the patient, this may be relayed to the patient.

If, at decision block 820, an update/message has not been received, then the method 800 returns to block 802 and proceeds as laid out above.

Figure 9:
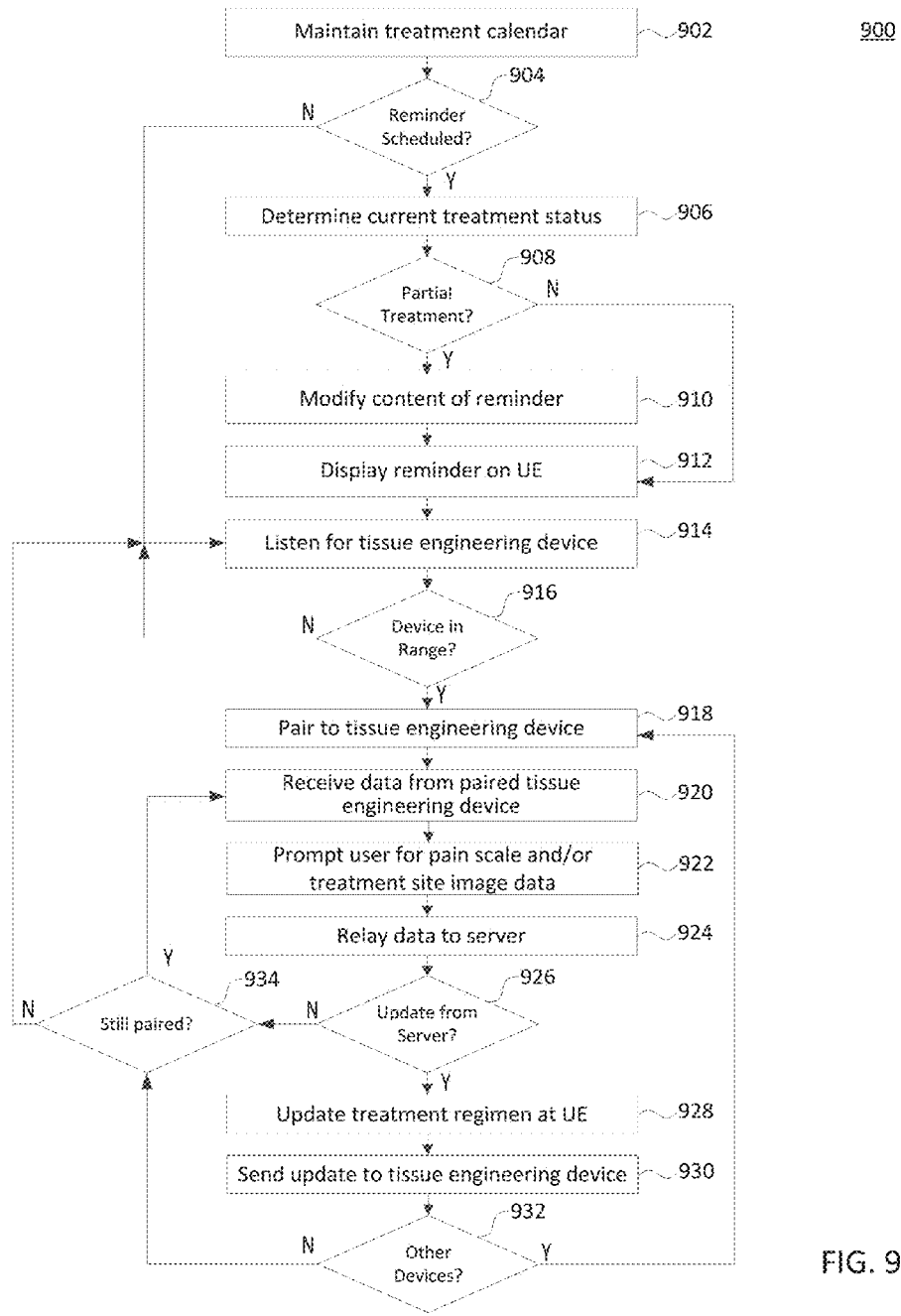
FIG. 9 is a flowchart illustrating an exemplary method for tissue treatment device compliance monitoring according to aspects of the present disclosure.

Turning now to FIG. 9, a flowchart illustrating an exemplary method 900 for tissue treatment device compliance monitoring is provided according to aspects of the present disclosure. In particular, the method 900 illustrates aspects of operation of the UE 104 according to embodiments of the present disclosure. For simplicity of discussion, description will be made with respect to a single tissue engineering device 102 in communication with the UE 104, as well as a single server 108, though it is understood that the UE 104 may be in communication with any number of tissue engineering devices 102 and/or any number of servers 108. It is understood that additional steps can be provided before, during, and after the steps of method 900, and that some of the steps described can be replaced or eliminated from the method 900.

At block 902, the UE 104 maintains a treatment calendar (e.g., via the compliance module 308 discussed with respect to FIG. 3 above). This may include tracking the treatment regimen in view of the current time of day, entering any reminders provided by a user of the UE 104/received from the server 108, providing the interactive interface for the calendar to the user of the UE 104, etc.

At decision block 904, if a reminder is scheduled, then the method 900 proceeds to block 906.

At block 906, the UE 104 determines a current treatment status for a tissue engineering device 102 associated with the UE 104 for a current periodic application of the long-term treatment regimen (e.g., treatment status for a given day of a multi-day treatment regimen). This includes accessing the most recent compliance data received from the tissue engineering device 102 (e.g., the monitoring data provided at block 606 of FIG. 6 or block 764 of FIG. 7B, which may include or be based on historical data) and comparing the compliance data to the treatment regimen (which may be stored locally or requested from the server 108).

At decision block 908, if partial treatment has occurred for the current periodic application of the treatment regimen, then the method 900 proceeds to block 910.

At block 910, the UE 104 modifies the content of a scheduled reminder for the patient/user of the UE 104, thereby implementing a dynamic alert. For example, where on a given day the patient completes the treatment prior to a time for which reminders are scheduled, the compliance module 308 may cancel the reminder for that day. If, however, the time of day that the treatment occurs is important, the compliance module 308 may allow the alert to be, instead of a typical alert to treatment, a reminder that the time of day of treatment is important (where applicable) to the treatment in addition to the periodicity and duration. Where treatment is partially completed for the day when the reminder is scheduled, the reminder may be modified in its content and/or intensity to account for the amount of treatment already determined to be completed (e.g., from data already received from a paired tissue engineering device 102).

Further, compliance over time (i.e., multiple periodic applications) may be taken into account when determining whether to dynamically modify the alert). Thus, for example, where the patient is compliant with treatment over time, the reminders may be minimized to a system tray reminder without audible and/or other visual alerts. If, however, the compliance is below a threshold, the alerts may become more aggressive, with audible alerts, changing volume (e.g., higher volume as percent compliant goes down over time), intrusive visual displays (e.g., to disrupt text reading), as well as potentially short audible reminders during phone use. The intensity of the reminders may increase as the level of compliance is determined to be decreasing over time, so as to encourage patient compliance with a treatment regimen designed for patient efficacy.

At block 912, the UE 104 displays the reminder as modified (if at all) from block 910 on a display of the UE 104. Further, or alternatively, the UE 104 may send the reminder as modified to the tissue engineering device 102 (where already paired to the tissue engineering device 102) to cause the tissue engineering device 102 display the reminder/alert.

Returning to decision block 908, if partial treatment has not occurred, then the method 900 proceeds to block 912 (with no dynamic modification of the reminder) and proceeds with displaying the reminder.

From block 912, the method 900 proceeds to block 914. At block 914, the UE 104 listens for the tissue engineering device 102 (or for any number of tissue engineering devices 102).

Returning to decision block 904, if no reminder is scheduled, then the method 900 proceeds to block 914 as laid out above.

From block 914, the method 900 proceeds to decision block 916. If no tissue engineering devices 102 are detected, or otherwise not in range of the UE 104, then the method returns to block 914 to continue listening for a tissue engineering device 102 to pair with (e.g., to receive monitoring data and/or send messages/updates received from the server 108). As used herein, listening for a tissue engineering device 102 includes embodiments where the tissue engineering device 102 includes a transceiver 212 and embodiments where the transceiver 212 is connected to the tissue engineering device 102 as part of a power supply or docking station (to name just a few examples).

If, instead, a tissue engineering device 102 is detected as in range, then the method 900 proceeds to block 918.

At block 918, the UE 104 pairs with the tissue engineering device 102. This pairing may occur according to a wired and/or wireless connection, such as any one or more connection types as discussed above.

At block 920, the UE 104 receives monitoring data from the tissue engineering device 102 that paired at block 918. This may include, in addition to the compliance monitoring data, impedance monitoring data used to estimate healing of the tissue.

At block 922, the UE 104 prompts the user of the UE 104 to input pain scale information with respect to the site of treatment (for example). Moreover, the UE 104 may prompt the user to also collect an image of the treatment site, whether on a periodic basis or in response to the pain scale information response exceeding a threshold (e.g., to make data available to assist a physician in determining whether an infection or other problem is occurring at the treatment site). This information may be collected at the same periodicity as the use of the tissue engineering device 102 specified in the treatment regimen. Although described with respect to FIG. 9 as occurring at the same time as the receipt of monitoring data from the tissue engineering device 102, the pain scale information and/or image collection prompting may occur according to a schedule that is unrelated to the receipt of monitoring data (though may still occur on a same periodic basis, such as daily, albeit not required to occur at the same time as the monitoring data is received). The prompt may occur with, e.g. be triggered by, the monitoring data received at block 920. Additional analysis may also be performed by the UE 104 to discover broader trends for the patient, such as identifying whether the patient is more sedentary or mobile during each treatment session. The information, including level of mobility, may be aggregated over time.

At block 924, the UE 104 relays the monitoring data received at block 920, as well as the pain scale information and/or image(s) of the treatment site received/collected at block 922 (and trend information, where determined/available) to the server 108 for storage in the server 108's database/compliance report generation. The UE 104 may relay the monitoring data when received, or according to a set schedule.

At decision block 926, if any update has been received from an access device 114 via server 108 (e.g., from the prescribing physician), then the method 900 proceeds to block 928. The update may be, for example, a change in the prescribed treatment regime (e.g., based on the prescribing physician reviewing a compliance report that may include both compliance and impedance monitor data, and pain scale information and/or image(s) of the treatment site) made via an access device 114 (and optionally routed through server 110).

At block 928, the UE 104 updates a copy of the treatment regimen maintained at the UE 104 as specified in the update received as identified at decision block 926. Where the update identified at decision block 926 is a message (e.g., from the prescribing physician), then the message may be displayed at the UE 104 if that is what is specified (e.g., instead of forwarding to the tissue engineering device 102).

At block 930, the UE 104 sends the update to the tissue engineering device 102 so that the treatment regimen may be updated there as well. Where the update identified at decision block 926 is a message (e.g., from the prescribing physician), then this may be relayed to the tissue engineering device 102 where that is what is specified (e.g., instead of displaying at the UE 104).

At decision block 932, if there are other tissue engineering devices 102 that were detected at block 914, the method 900 may return to block 918 and proceed as discussed above and below. This may occur, for example, where the UE 104 is associated with a physician or representative of the manufacturer that may have opportunity to pair with multiple devices.

If, at decision block 932, there are not other tissue engineering devices 102 that can be, or should be, paired with, then the method 900 proceeds to decision block 934.

Returning to decision block 926, if no update/message has been received from the server 108, then the method 900 proceeds to decision block 934.

At decision block 934, if the UE 104 is still paired with the tissue engineering device 102, then the method 900 returns to block 920 to continue receiving data. If, instead, the tissue engineering device 102 is no longer paired, then the method 900 returns to block 914 to listen for tissue engineering devices 102 as laid out above.

Through all of this in method 900, the steps laid out at blocks 902 through 912 may continue to occur over time, whether concurrent to pairing with any devices or otherwise.

In some embodiments, the computing system is programmable and is programmed to execute processes including the processes of methods 600, 700, 750, 800 and/or 900 discussed herein. Accordingly, it is understood that any operation of the computing system according to the aspects of the present disclosure may be implemented by the computing system using corresponding instructions stored on or in a non-transitory computer readable medium accessible by the processing system. For the purposes of this description, a tangible computer-usable or computer-readable medium can be any apparatus that can store the program for use by or in connection with the instruction execution system, apparatus, or device. The medium may include for example non-volatile memory including magnetic storage, solid-state storage, optical storage, cache memory, and Random Access Memory (RAM).

As a result of implementing the above-described approach, embodiments of the present disclosure improve the field of pulsed electromagnetic field therapy for tissue engineering, such as for tissue differentiation and/or growth stimulation of tissue. In particular, embodiments of the present disclosure improve the transparency of treatment compliance so that more efficacious treatment regimens may be provided and prescribed to patients, whether at the onset of treatment or dynamically during treatment. The tissue engineering device itself may therefore be tuned to operate more efficiently for a given indication within a prescribed period of time as is now otherwise possible. This may therefore further improve clinical success rates of PEMF tissue engineering devices while still providing an energy-efficient tissue engineering device that is convenient for the patient to use according to prescribed usage.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A musculoskeletal tissue engineering and compliance monitoring system, comprising:

a tissue engineering apparatus comprising a coil device configured to supply a pulsed electromagnetic field (PEMF) to musculoskeletal tissue, wherein the tissue engineering apparatus is configured with a treatment regimen defining a periodic application of the PEMF over a long-term duration, the tissue engineering apparatus further comprising a sensor configured to detect use of the tissue engineering apparatus on the musculoskeletal tissue and a first transceiver configured to transmit data from the sensor;

a user equipment (UE) device comprising a second transceiver configured to associate with the tissue engineering apparatus and receive the data from the tissue engineering apparatus, and a UE processor configured to compare the data for compliance with the periodic application specified in the treatment regimen, generate a current status of the periodic application, and modify a treatment reminder based on the current status of the periodic application; and a remote server comprising a third transceiver configured to receive the data including the current status from the UE device, and a server processor configured to compile the data into a compliance report identifying use of the tissue engineering apparatus over the long-term duration, the third transceiver further configured to transmit the compliance report to a subscribing device.

2. The musculoskeletal tissue engineering and compliance monitoring system of claim 1, wherein the UE processor is further configured to:
cause a display of the UE device to provide the treatment reminder according to the periodic application defined in the treatment regimen; and
determine whether the PEMF has already been supplied for a given periodic application over the long-term duration, and an extent of supply having already occurred for the given periodic application,
wherein the modification further comprises modifying the treatment reminder according to the extent determined for supply having already occurred for the given periodic application.

3. The musculoskeletal tissue engineering and compliance monitoring system of claim 1, wherein:
the tissue engineering apparatus further comprises an impedance monitor sensor,
the impedance monitor sensor is configured to detect a plurality of tissues including the musculoskeletal tissue, wherein the data corresponds to a stage of healing of the musculoskeletal tissue based on the detected plurality of tissues,
the tissue engineering apparatus is further configured to determine and display a level of compliance with respect to the treatment regimen, the data including the determined level of compliance, and
the first transceiver is further configured to transmit the data to the remote server for inclusion in the compliance report.

4. The musculoskeletal tissue engineering and compliance monitoring system of claim 1, wherein the server processor is further configured to:
aggregate the data received via the UE device from the tissue engineering apparatus during a period according to a periodic basis;
generate the compliance report at an end of the period; and
cause the remote server to provide a reminder about the treatment regimen based on a result of a comparison of data from the compliance report with the treatment regimen.

5. The musculoskeletal tissue engineering and compliance monitoring system of claim 1, wherein the subscribing device comprises a plurality of devices including the UE device and one or more computing devices configured to be associated with one or more physicians, the third transceiver further configured to transmit a notification to at least one of the plurality of devices that is based on the compliance report.

6. The musculoskeletal tissue engineering and compliance monitoring system of claim 1, wherein the periodic application is on a per-day basis, and the compliance report comprises:
a number of days that the tissue engineering apparatus has been in possession;
a breakdown of use of the tissue engineering apparatus per day for the number of days; and
a percentage of compliance based on the data and the treatment regimen.

7. The musculoskeletal tissue engineering and compliance monitoring system of claim 1, wherein the UE processor is further configured to:
receive, via a user interface of the UE, a pain scale value corresponding to a level of pain associated with a treatment site with the musculoskeletal tissue;
receive, via the user interface, an image of the treatment site; and
transmit the pain scale value and the image to the remote server for inclusion in the compliance report.

8. The musculoskeletal tissue engineering and compliance monitoring system of claim 1, wherein:
the server processor is further configured to instruct, in response to the identifying the use of the tissue engineering apparatus over the long-term duration as deviating from the treatment regimen, the UE device to adjust one or more of a frequency of reminders, audible tones, verbal messages, text reminders, and interactive text-based messages until the deviating decreases below a threshold, and
the UE processor is further configured, based on the instruction, to adjust the one or more of the frequency of reminders, audible tones, verbal messages, text reminders, and interactive text-based messages.

9. An apparatus for musculoskeletal tissue engineering and compliance monitoring, comprising:
a tissue engineering device comprising a transducer coil configured to supply a pulsed electromagnetic field to musculoskeletal tissue;
a sensor configured to detect proximity of the tissue engineering device to the musculoskeletal tissue determined to correspond to application of the tissue engineering device to the musculoskeletal tissue;
a processor configured to poll the sensor for data identifying whether the tissue engineering device is in proximity and attributable to use of the apparatus with the musculoskeletal tissue; and
a transceiver configured to transmit the data to a separate device configured to determine compliance in using the apparatus according to a treatment regimen comprising a periodic activation over a defined number of applications, and to receive an update to the treatment regimen in response to the data being transmitted to the separate device and a remote server, based on a command provided by a computer device that is in communication with the remote server.

10. The apparatus of claim 9, wherein:
the sensor comprises an accelerometer,
the poll comprises a first poll period having a first duration that is less than a duration of the periodic activation, wherein the accelerometer detecting motion during the first poll period indicates a first affirmative status of compliance for the first poll period, and
the data transmitted by the transceiver comprises the first affirmative status.

11. The apparatus of claim 10, wherein:
the poll further comprises a second poll period having a second duration that is larger than and includes the first duration including a first plurality of first poll periods, and a third poll period having a third duration that is larger than, and includes, the second duration including a second plurality of first poll periods that includes the first plurality of first poll periods, the second and third durations being less than the duration of the periodic activation,
the accelerometer detecting motion during the second poll period for at least half of the first plurality of first poll periods, comprised in the second poll period, indicates a second affirmative status of compliance for the second poll period, the accelerometer detecting motion during the third poll period for at least a quarter of the second plurality of first poll periods, comprised in the third poll period, indicates a third affirmative status of compliance for the third poll period, and the data transmitted by the transceiver comprises the third affirmative status.

12. The apparatus of claim 9, wherein the transceiver is further configured to receive a current time of day from the separate device after pairing with the separate device.

13. The apparatus of claim 9, wherein the transceiver is further configured to transmit the data to the remote server via the separate device.

14. The apparatus of claim 13, further comprising a display, wherein the processor is further configured to generate a compliance indication based on the data in comparison to the treatment regimen and to output the compliance indication on the display.

15. The apparatus of claim 9, further comprising a healing monitor sensor, wherein:

the healing monitor sensor is configured to detect a plurality of tissues including the musculoskeletal tissue, the processor is further configured to poll the healing monitor sensor for sensed data corresponding to the detected plurality of tissues, wherein the sensed data corresponds to a stage of healing of the musculoskeletal tissue, and the transceiver is further configured to transmit the sensed data for inclusion in a compliance report that comprises the sensed data, a pain scale value, an image of a treatment site with the musculoskeletal tissue, and an activity level.

* * * * *